US007879571B2

(12) United States Patent
Harding

(10) Patent No.: US 7,879,571 B2
(45) Date of Patent: Feb. 1, 2011

(54) POPULATION BASED ASSESSMENTS AND MEANS TO RANK THE RELATIVE IMMUNOGENICITY OF PROTEINS

(75) Inventor: Fiona A. Harding, Santa Clara, CA (US)

(73) Assignee: Danisco US Inc., Palo Alto, CA (US)

(*) Notice: Subject to any disclaimer, the term of this patent is extended or adjusted under 35 U.S.C. 154(b) by 468 days.

(21) Appl. No.: 10/502,818

(22) PCT Filed: Feb. 26, 2003

(86) PCT No.: PCT/US03/05670

§ 371 (c)(1),
(2), (4) Date: Mar. 7, 2005

(87) PCT Pub. No.: WO03/073068

PCT Pub. Date: Sep. 4, 2003

(65) Prior Publication Data

US 2005/0158806 A1    Jul. 21, 2005

(51) Int. Cl.
*C12N 5/078* (2010.01)
*G01N 33/53* (2006.01)
(52) U.S. Cl. .................................. 435/7.24; 435/377
(58) Field of Classification Search .................... None
See application file for complete search history.

(56) References Cited

U.S. PATENT DOCUMENTS

| | | | |
|---|---|---|---|
| 4,261,868 A | 4/1981 | Hora et al. | 252/529 |
| 4,404,128 A | 9/1983 | Anderson | 252/546 |
| 4,533,359 A | 8/1985 | Kondo et al. | 8/128 R |
| 4,760,025 A | 7/1988 | Estell et al. | 435/222 |
| 5,185,258 A | 2/1993 | Caldwell et al. | 435/220 |
| 5,204,015 A | 4/1993 | Caldwell et al. | 252/174.12 |
| 5,627,025 A | 5/1997 | Steinman et al. | |
| 5,691,147 A | 11/1997 | Draetta et al. | |
| 5,710,126 A * | 1/1998 | Griffith et al. | 514/12 |
| 5,804,201 A * | 9/1998 | King | 424/275.1 |
| 6,110,695 A | 8/2000 | Gunn et al. | |
| 6,218,165 B1 | 4/2001 | Estell et al. | 435/221 |
| 6,451,316 B1 | 9/2002 | Srivastava | |
| 6,861,234 B1 * | 3/2005 | Simard et al. | 435/29 |

FOREIGN PATENT DOCUMENTS

| | | |
|---|---|---|
| EP | 0 279 994 A | 8/1988 |
| EP | 0 134 267 B1 | 8/1989 |
| WO | WO 89/04552 | 5/1989 |
| WO | WO 89/06279 | 7/1989 |

OTHER PUBLICATIONS

Stickler et al, Jour. Immunological Methods, vol. 281, pp. 95-108, 2003.*

Alexander et al., "The Optimization of Helper T Lymphocyte (HTL) Function in Vaccine Development," *Immunologic Research*, 18/2:79-92 (1998).
Altschul et al., "Basic Local Alignment Search Tool," *J. Mol. Biol.*, 215:403-410 (1990).
Altschul et al., "Local Alignment Statistics," *Meth. Enzymol.*, 266:460-480 (1996).
Altuvia et al., "Ranking Potential Binding Peptides to MHC Molecules by a Computational Threading Approach," *J. Mol. Biol.*, 249:244-250 (1995).
Asai et al., "Evaluation of the Modified ELISPOT Assay for Gamma Interferon Production in Cancer Patients Receiving Antitumor Vaccines," *Clinical and Diagnostic Laboratory Immunology*, 7(2):145-154 (2000).
Asquith et al., "Lymphocyte Kinetics: The Interpretation of Labelling Data," *Trends in Immunology*, 23(12):596-601 (2002).
Berzofsky, "Epitope Selection and Design of Synthetic Vaccines," *Annals New York Academy of Sciences*, 690:256-264 (1993).
Black et al., "HLA-DQ Determines the Response to Exogenous Wheat Proteins: A Model of Gluten Sensitivity in Transgenic Knock-out Mice" *The Journal of Immunology*, 169:5595-5600 (2002).
Blaikie et al., "Experience with a Mouse Inranasal Test for the Predictive Identification of Respiratory Sensitization Potential of Proteins," *Food and Chemical Toxicology*, 37:889-896 (1999).
Boyton et al., "Transgenic Models of Autoimmune Disease," *Clin. Exp. Immunol.*, 127:4-11 (2002).
Casadevall et al., "Pure Red-Cell Aplasia and Antierythropoietin Antibodies in Patients Treated with Recombinant Erythropoietin," *The New England Journal of Medicine*, 346(7):469-475 (2002).
Das et al., "HLA Transgenic Mice as Models of Human Autoimmune Diseases," *Reviews in Immunogenetics*, 2:105-114 (2000).
Devereux et al., "A Comprehensive Set of sequence Analysis Programs for the VAX," *Nucleic Acids Research*, 12(1):387-395 (1984).
Doolan et al., "HLA-DR-Promiscuous T Cell Epitopes from *Plasmodium falciparum* Pre-Erythrocytic-Stage Antigens Restricted by Multiple HLA Class II Alleles," *The Journal of Immunology*, 165:1123-1137 (2000).
Farrar et al., "Selective Loss of type I Interferon-Induced STAT4 Activation Caused by a Minisatellite Insertion in Mouse Stat2," *Nature Immunology*, 1(1):65-69 (2000).
Feng et al., "Progressive Sequence Alignment as a Prerequisite to Correct Phylogenetic Trees," *J. Mol. Evol.*, 25:351-360 (1987).
Goldsborough et al., "A Comparison Study of Human Papillovavirus Prevalence by the Polymerase Chain Reaction in Low Risk Women and in a Gynaecology Referral Group at elevated Risk for Cervical Cancer," *Molecular and Cellular Probes*, 6:451-457 (1992).

(Continued)

*Primary Examiner*—David A Saunders

(57) ABSTRACT

The present invention provides means to assess immune response profiles of populations. In particular, the present invention provides means to qualitatively assess the immune response of human populations wherein the immune response directed against any protein of interest is analyzed. The present invention further provides means to rank proteins based on their relative immunogenicity. In addition, the present invention provides means to create proteins with reduced immunogenicity for use in various applications.

37 Claims, 14 Drawing Sheets

OTHER PUBLICATIONS

Guéry et al., "Constitutive Presentation of Dominant Epitopes from Endogenous Naturally processed Self-β-Microglobulin to Class II-Restricted T Cells Leads to Self-Tolerance," *The Journal of Immunology*, 154:545-554 (1995).
Henikoff et al., "Amino Acid Substitution Matarices from Protein Blocks," *Proc. Natl. Acad. Sci. USA*, 89:10915-10919 (1992).
Hesse et al., "A T Cell Clone's Avidity is a Function of Its Activation State," *The Journal of Immunology*, 167:1353-1361 (2001).
Higgins et al., "Fast and Sensitive Multiple Sequence alignments on a Microcomputer," *Cabios Communications*, 5(2):151-153 (1989).
Imamura et al., "Cloning and Characterization of a Human DEAH-Box RNA Helicase, a Functional Homolog of Fission Yeast Cdc28/Prp8," *Nucleic Acids Research*, 26(9):2063-2068 (1998).
Karlin et al., "Applications and Statistics for Multiple High-scoring Segments in Molecular Sequences," *Proc. Natl. Acad. Sci. USA*, 90:5873-5877 (1993).
Keilholz et al., "Immunologic Monitoring of Cancer Vaccine Therapy: Results of a Workshop Sponsored by the Society for Biological Therapy," *Journal of Immunotherapy*, 25(2):97-138 (2002).
Kim et al., "Constraints in Antigen Processing Result in Unresponsiveness to a T Cell Epitope of Hen Egg Lysozyme in C57BL/6 Mice," *Eur. J. Immunol.*, 22:775-782 (1992).
Kimber et al., "Toxicology of Protein Allergenicity: Prediction and Characterization," *Toxicological Sciences*, 48:157-162 (1999).
Kimber et al., "Identification of Respiratory Allergens," *Fundamental and Applied Toxicology*, 33:1-10 (1996).
Krco et al., "Identification of T Cell Determinants on Human Type II Collagen Recognized by HLA-DQ8 and HLA-DQ6 Transgenic Mice," *The Journal of Immunology*, 163:1661-1665 (1999).
Kuhns et al., "Cytotoxic T Lymphocyte Antigen-4 (CTLA-4) Regulates the Size, Reactivity, and Function of a Primed Pool of CD4$^+$ T Cells," *PNAS*, 97(23):12711-12716 (2000).
Lazcano-Ponce et al., "Epidemiology of HPV Infection Among Mexican Women with Normal Cervical Cytology," *Int. J. Cancer*, 91:412-420 (2001).
Li et al., "Thrombocytopenia Caused by the Development of Antibodies to Thrombopoietin," *Blood*, 98(12):3241-3248 (2001).
Lorincz et al., "Human Papillomavirus Infection of the Cervix : Relative Risk Associations of 15 Common Anogenital Types," *Obsterics & Gynecology*, 79:328-337 (1992).
Maeji et al., "Multi-pin Peptide Synthesis Strategy for T Cell Determinant Analysis," *Journal of Immunological Methods*, 134:23-33 (1990).
Manici et al.,"Melanoma Cells Present a MAGE-3 Epitope to DC4+ Cytotoxic T Cells in Association with Histocompatibility Leukocyte Antigen DR11," *J. Exp. Med.*, 189(5):871-876 (1999).
Matthies, "Allergies by Detergents and Cleansing Products: Facts and Figures," *Tenside Surf. Det.*, 34:450-454 (1997).
Mori et al., "HLA Gene and Haplotype Frequencies in the North American Population: The National Marrow Donor Program Donor Registry," *Transplantation*, 64:1017-1027 (1997).
Mucha et al., "Enhanced Immunogenicity of a Functional Enzyme by T Cell Epitope Modification," *BMC Immunology*, 3:1471-2172 (2002).
Muraro et al., "Human Autoreactive CD4$^+$ T Cells from Naive CD45RA$^+$ and Memory CD45RO$^+$ Subsets Differ with Respect to Epitope Specificity and Functional Antigen Avidity," *The Journal of Immunology*, 164:5474-5481 (2000).
Needleman et al., "A General Method Applicable to the Search for Similarities in the Amino Acid Sequence of Two Proteins," *J. Mol., Biol.*, 48:443-453 (1970).
Novitsky et al., "Magnitude and Frequency of Cytotoxic T-Lymphocyte Responses: Identification of Immunodominant Regions of Human Immunodeficiency Virus Type 1 Subtype C," *Journal of Virology*, 76(20):10155-10168 (2002).
Olsson et al., "Antigenicity of Mouse Monoclonal Antibodies. A Study on the Variable Region of the Heavy Chain," *J. Theor. Biol.*, 151:111-122 (1991).
Pathan et al., "Direct Ex Vivo Analysis of Antigen-Specific IFN-γ-Secreting CD4 T Cells in *Mycobacterium Tuberculosis*-Infected Individuals: Associations with Clinical Disease State and Effect of Treatment," *The Journal of Immunology*, 167:5217-5225 (2001).

Pearson et al., "Improved Tools for Biological Sequence Comparison," *Proc. Natl. Acad. Sci. USA*, 85:2444-2448 (1988).
Rachmilewitz et al., "A Temporal and Spatial Summation Model for T-Cell Activiation: Signal Integration and Antigen Decoding," *Trends in Immunology*, 23(12):592-595 (2002).
Raju et al., "Cryptic Determinants and Promiscuous Sequences on Human Acetylcholine Receptor: HLA-Dependent Dichotomy in T-Cell Function," *Human Immunology*, 63:237-247 (2002).
Rammensee et al., "SYFPEITHI: Database for MHC Ligands and Peptide Motifs," *Immunogenetics*, 50:213-219 (1999).
Robinson et al., "Use of the Mouse Intranasal Test (MINT) to Determine the Allergenic Potency of Detergent Enzymes: Comparison to the Guinea Pig Intratracheal (GPIT) Test," *Toxicological Sciences*, 43:39-46 (1998).
Sarlo et al., "Respiratory Allergenicity of Detergent Enzymes in the Guinea Pig Intratracheal Test: Association with Sensitization of Occupationally Exposed Individuals," *Fundamental and Applied Toxicology*, 39:44-52 (1997).
Sarlo et al., "Occupational Asthma and Allergy in the Detergent Industry: New Developments," *Current Opinion in Allergy Clinical Immunology*, 2:97-101 (2002).
Sayre et al., "Physical Sunscreens," *J. Soc. Cosmet. Chem.*, 41:103-109 (1990).
Scagnolari et al., "Neutralizing and Binding Antibodies to IFN-β: Relative Frequency in Relapsing-Remitting Multiple Sclerosis Patients Treated with Different IFN-β Preparations," *Journal of Interferon and Cytokine Research*, 22:207-213 (2002).
Schweigert et al., "Occupational Asthma and Allergy Associated with the Use of Enzymes in the Detergent Industry—a Review of the Epidemiology, Toxicology and Methods of Prevention," *Clinical and Experimental Allergy*, 30:1511-1518 (2000).
Sicherer et al., "Peanut and Tree Nut Allergy," *Current Opinion in Pediatrics*, 12:567-573 (2000).
Smith et al., "Comparison of Biosequences," *Advances in Applied Mathematics*, 2:482-489 (1981).
Southwood et al., "Several Common HLA-DR Types Share Largely Overlapping Peptide Binding Repertoires," *The Journal of Immunology*, 160:3363-3373 (1998).
Stickler et al., "CD4+ T-Cell Epitope Determination Using Unexposed Human Donor Peripheral Blood Mononuclear Cells," *Journal of Immunotherapy*, 23(6):654-660 (2000).
Stickler et al., "An In vitro Human Cell-Based Assay to Rank the Relative Immunogenicity of Proteins," *Toxicology Sciences*, 77:280-289 (2004).
Stone et al., "Seroprevalence of Human Papillomavirus Type 16 Infection in the United States," *The Journal of Infectious Diseases*, 186:1396-1402 (2002).
Sturniolo et al., "Generation of Tissue-Specific and Promiscuous HLA Ligand Databases Using DNA Microarrays and Virtual HLA Class II Matrices," *Nature Biotechnology*, 17:555-561 (1999).
Vanderlugt et al., "Epitope Spreading in Immune-Mediated Diseases: Implications for Immunotherapy," *Nature Reviews*, 21:85-95 (2002).
Vanderlugt et al., "Pathologic Role and Temporal Appearance of Newly Emerging Autoepitopes in Relapsing Experimental Autoimmune Encephalomyelitis," *The Journal of Immunology*, 164:670-678 (2000).
Viola et al., "T Cell Activation Determined by T Cell Receptor Number and Tunable Thresholds," *Science*, 273:104-106 (1996).
Warmerdam et al., "Staphylokinase-Specific Cell-Mediated Immunity in Humans," *The Journal of Immunology*, 168:155-161 (2002).
Yin et al., "Induction of Species-Specific Host Accommodation in the Hamster-to-Rat Xenotransplantation Model," *The Journal of Immunology*, 161:2044-2051 (1998).
Yu et al., "Methods for Prediction of Peptide Binding to MHC Molecules: A Comparative Study," *Molecular Medicine*, 8(3):137-148 (2002).
Kotz and Johnson (eds.) (1982) *Encyclopedia of Statistical Sciences*, vol. 2, John Wiley and Sons, New York, NY. Bibliographic pages and pp. 512-516.
Kotz and Johnson (eds.) (1988) *Encyclopedia of Statistical Sciences*, vol. 9, John Wiley and Sons, New York, NY. Bibliographic pages and p. 300.

\* cited by examiner

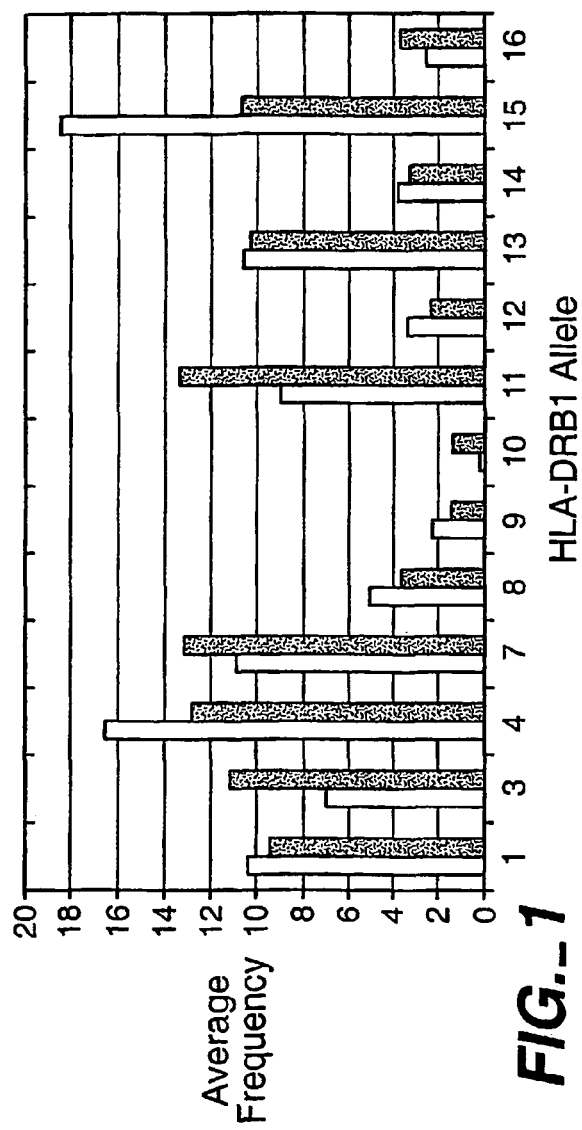
FIG._1

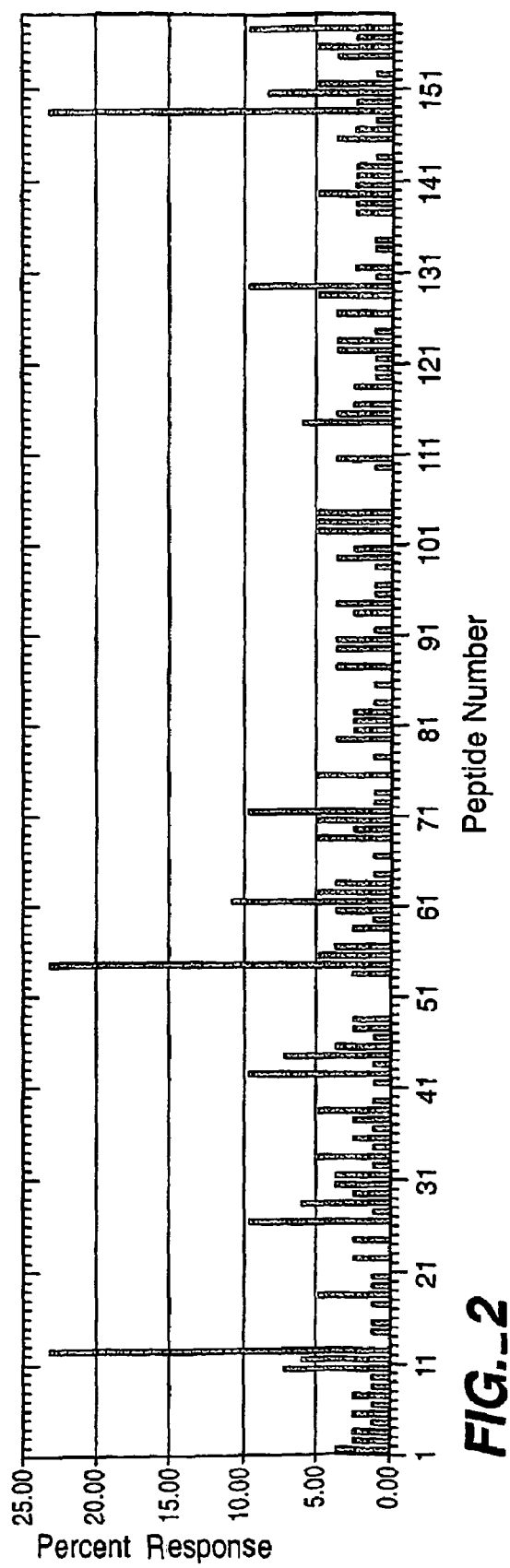
FIG._2

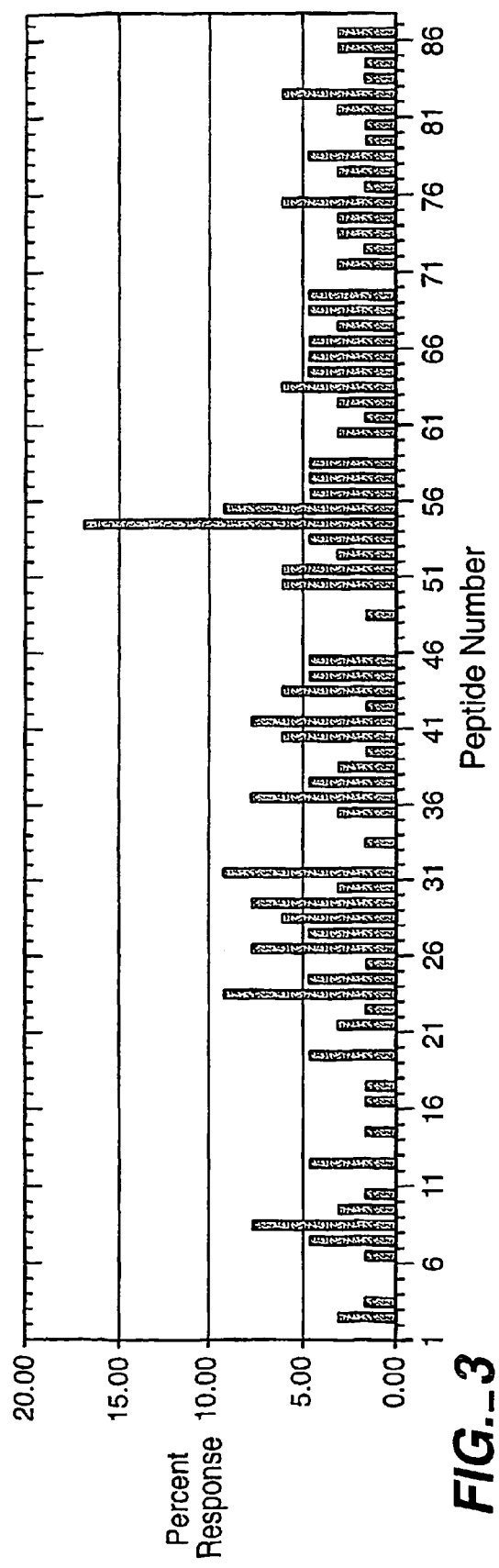
FIG._3

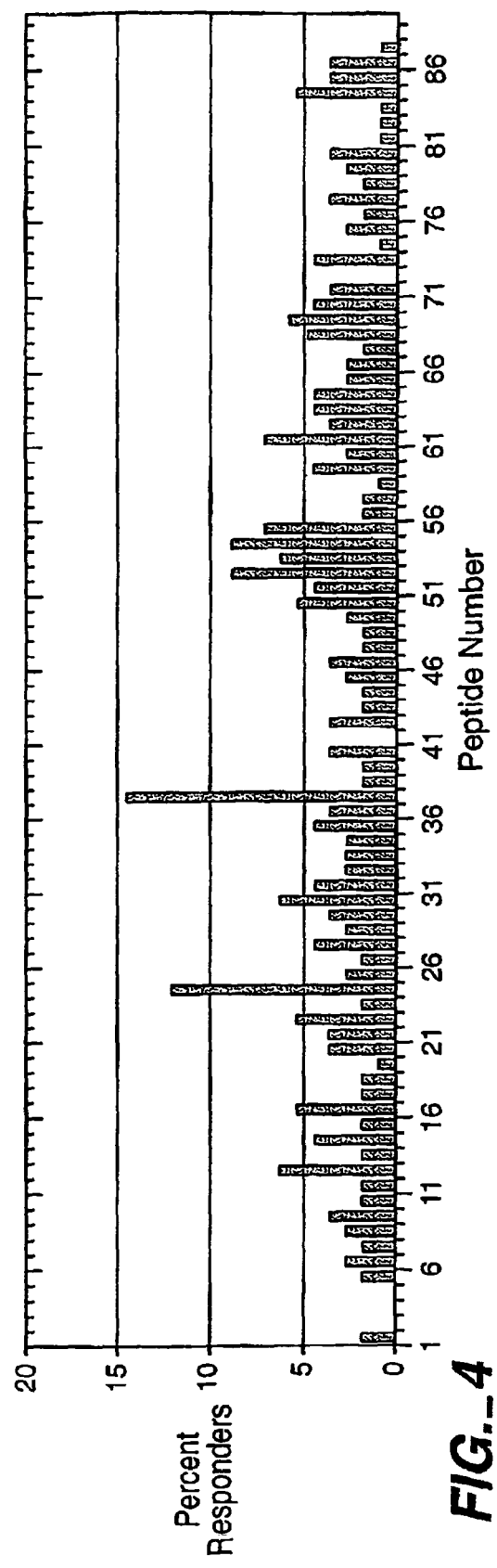
FIG._4

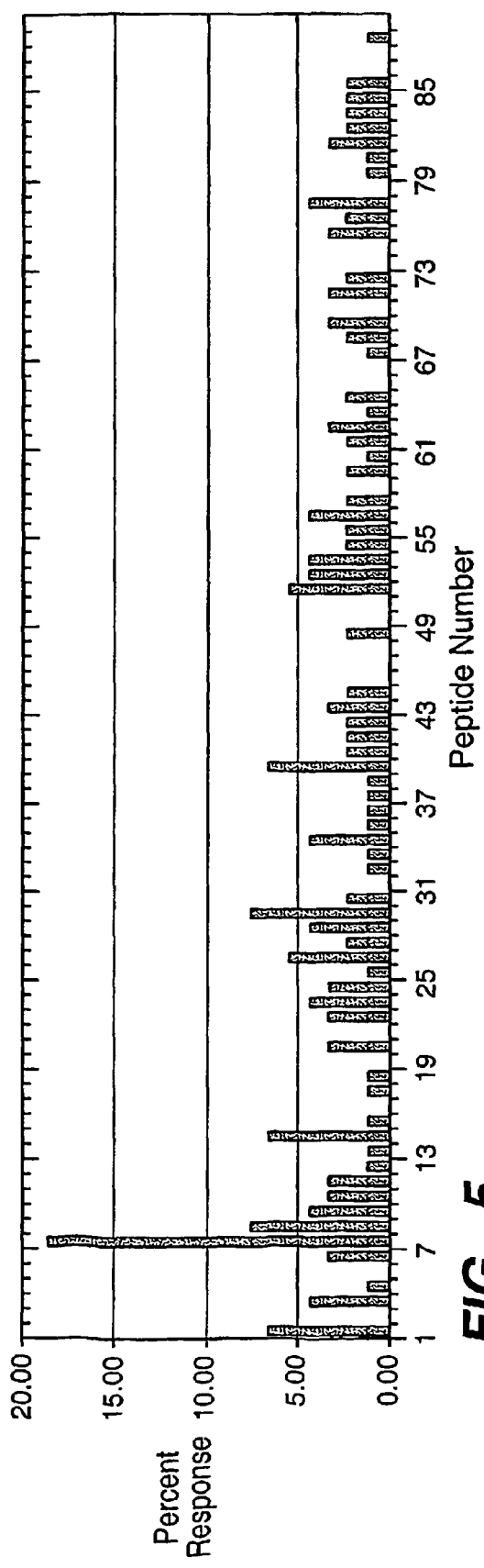
FIG._5
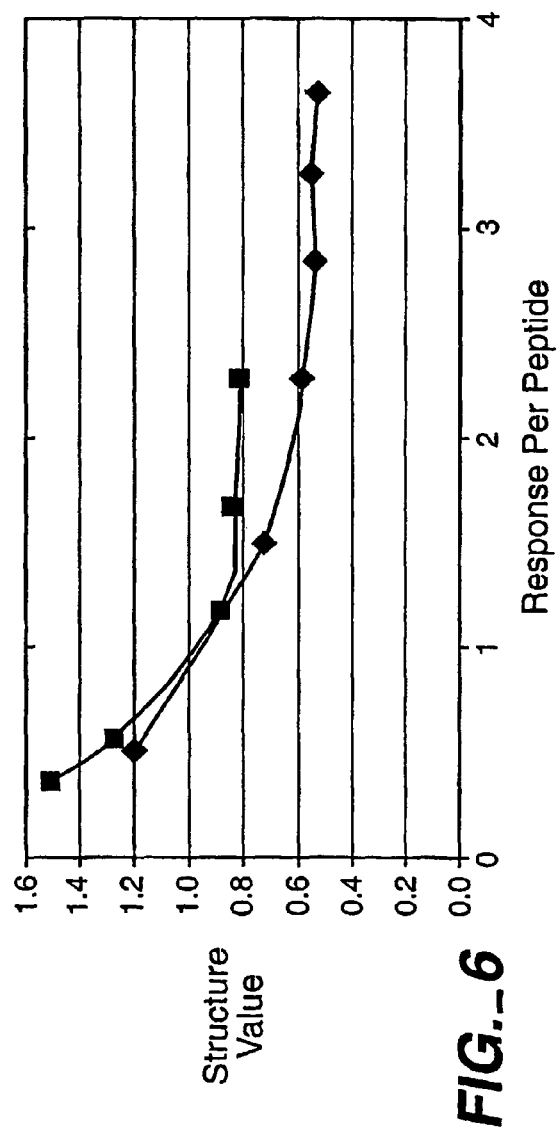
FIG._6

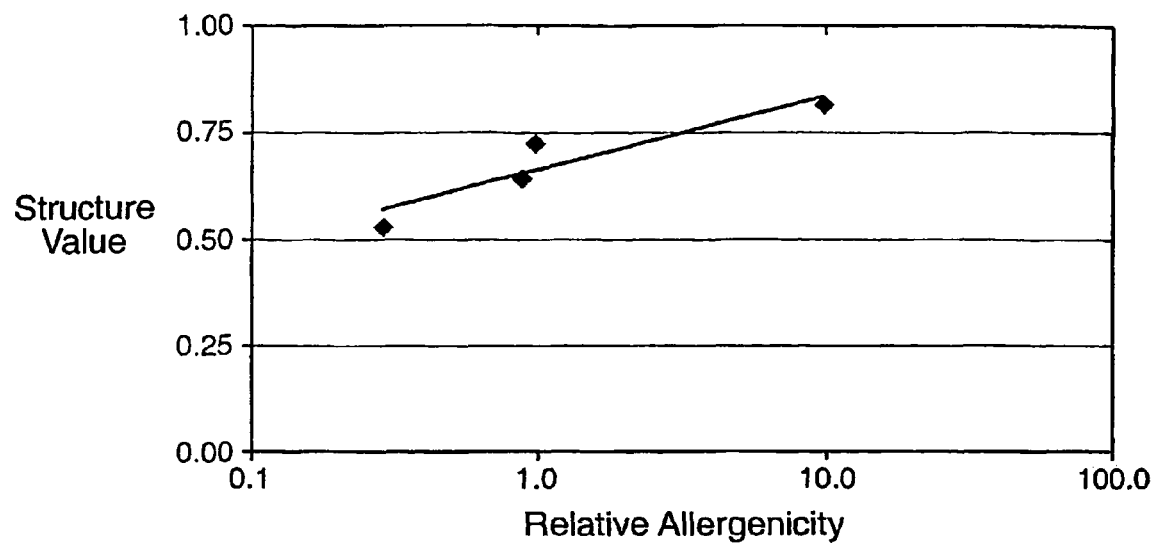
FIG._7A
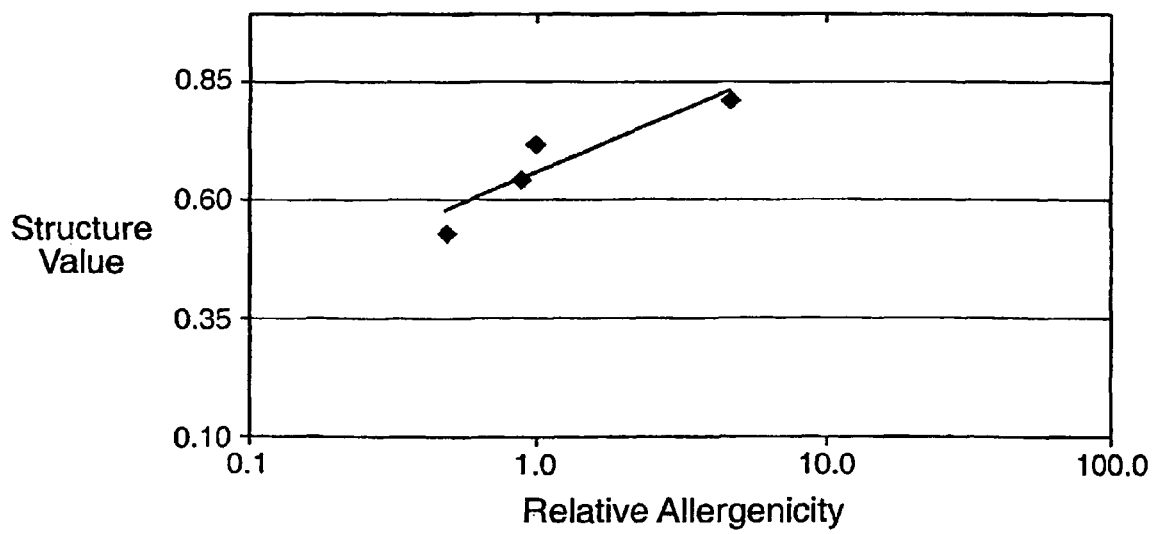
FIG._7B

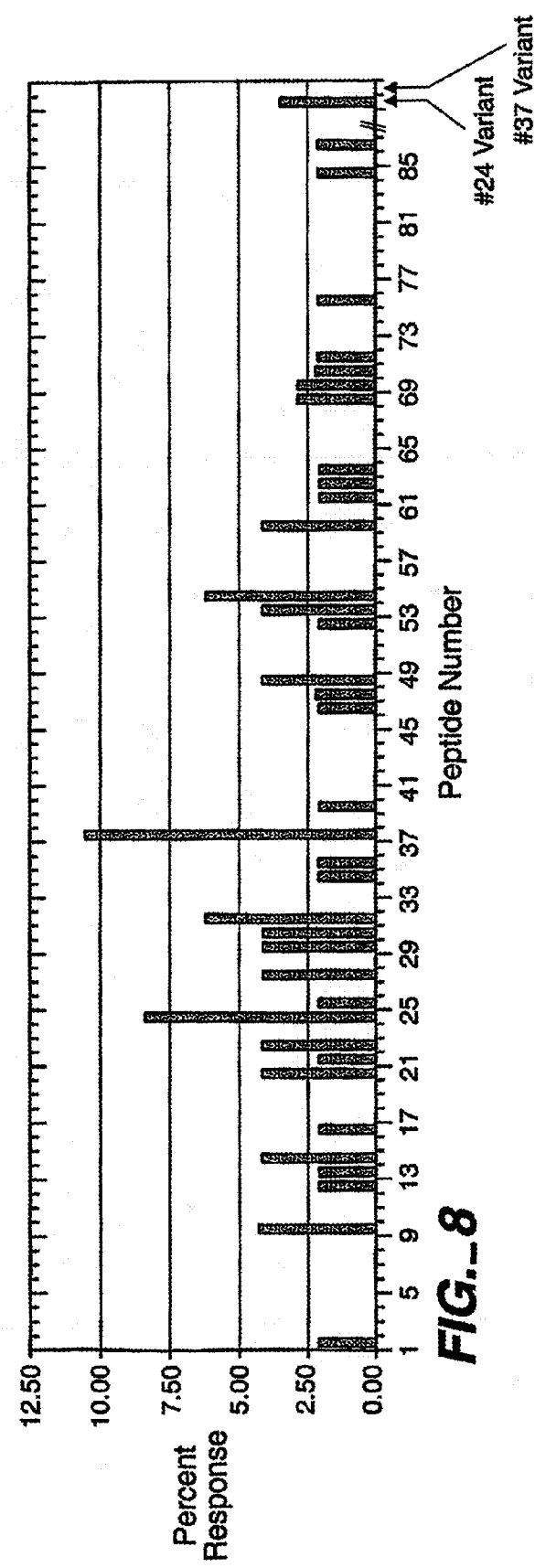
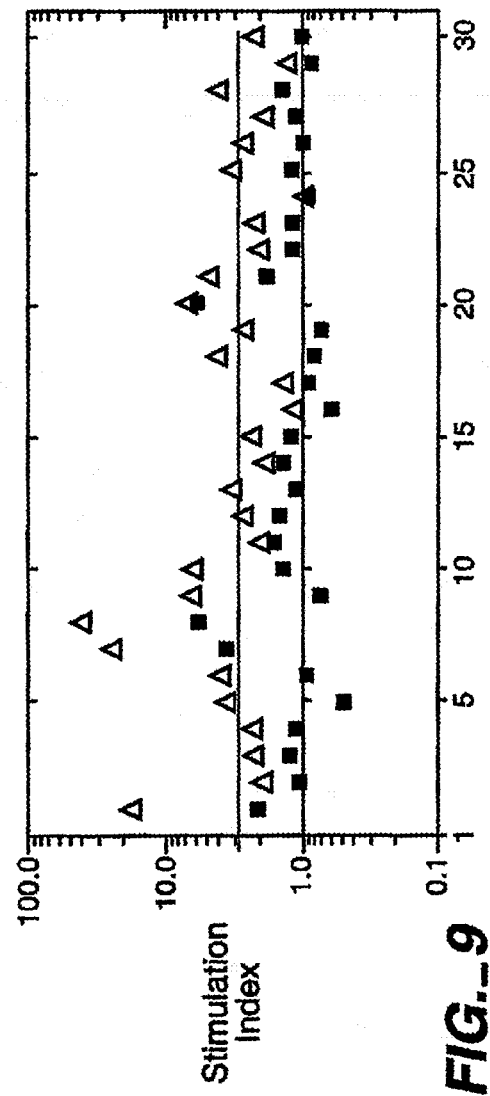
FIG._8
FIG._9

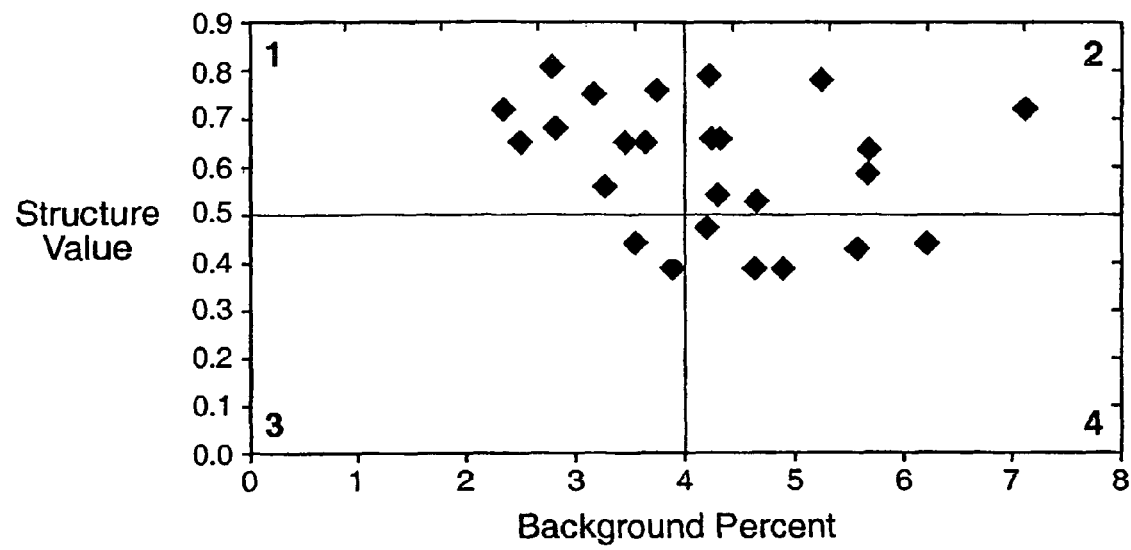
FIG._10
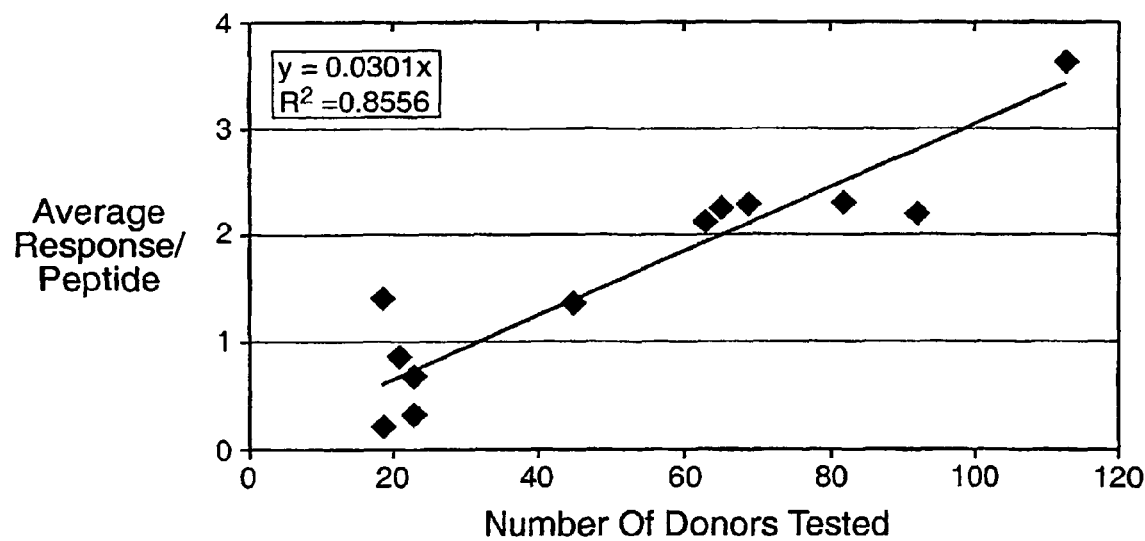
FIG._11

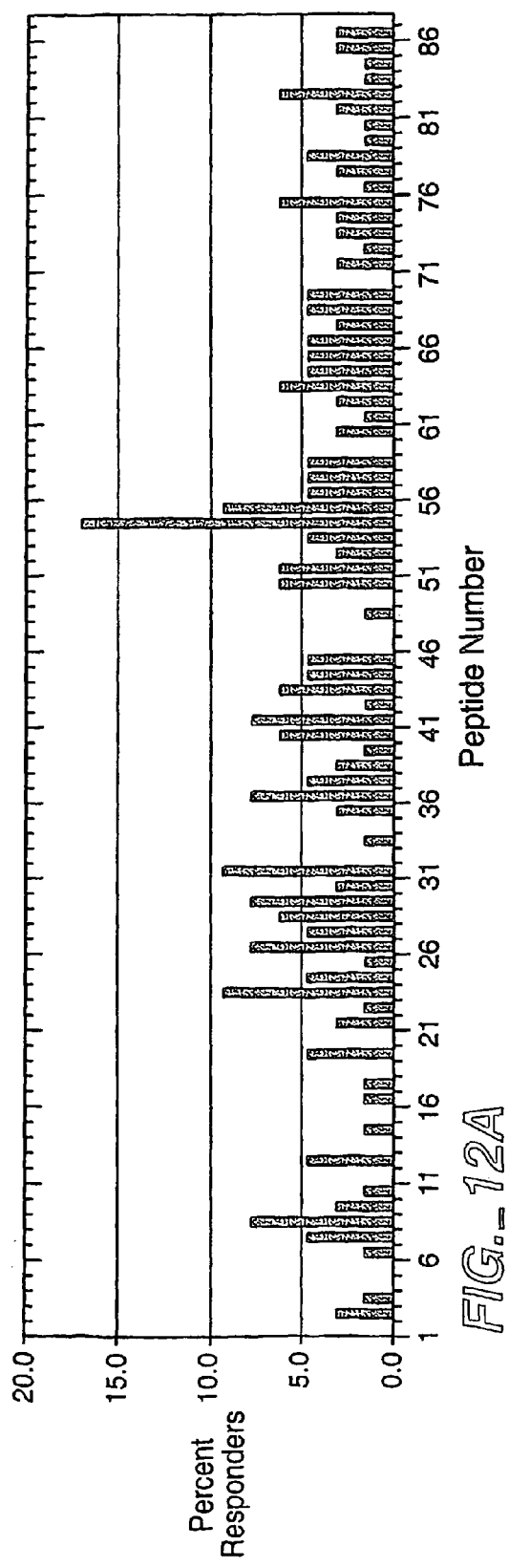
FIG._12A
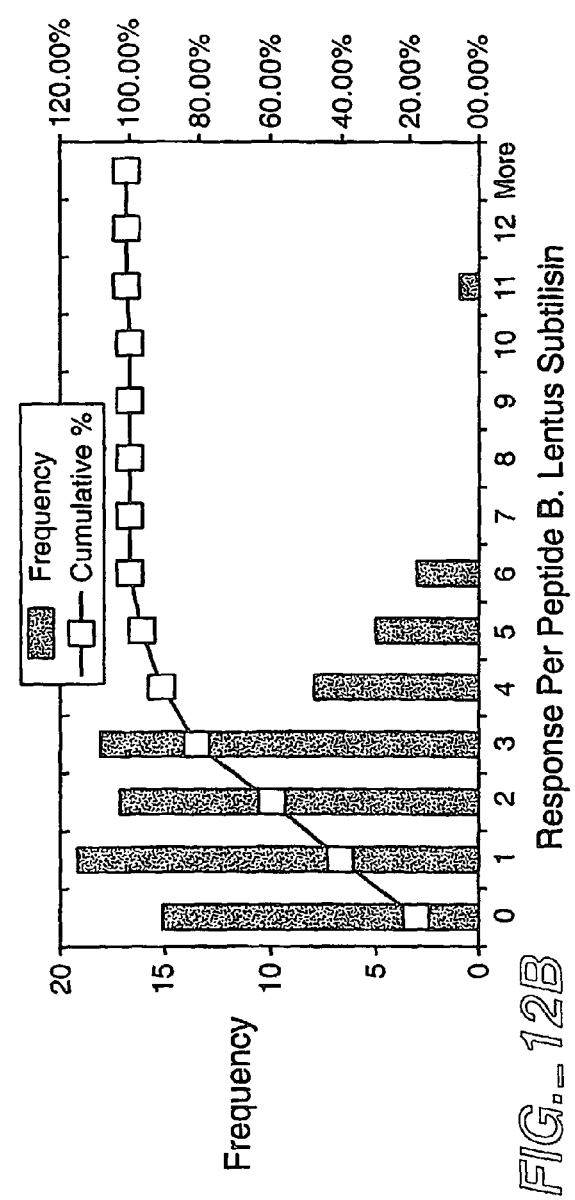
FIG._12B

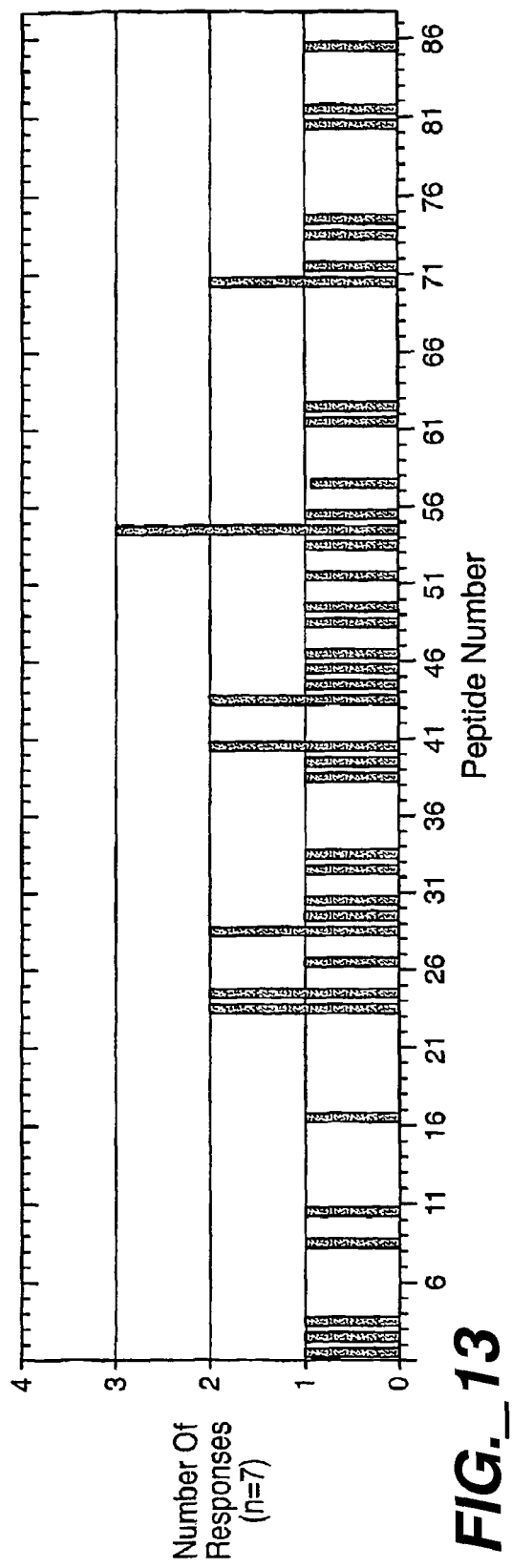
FIG._13

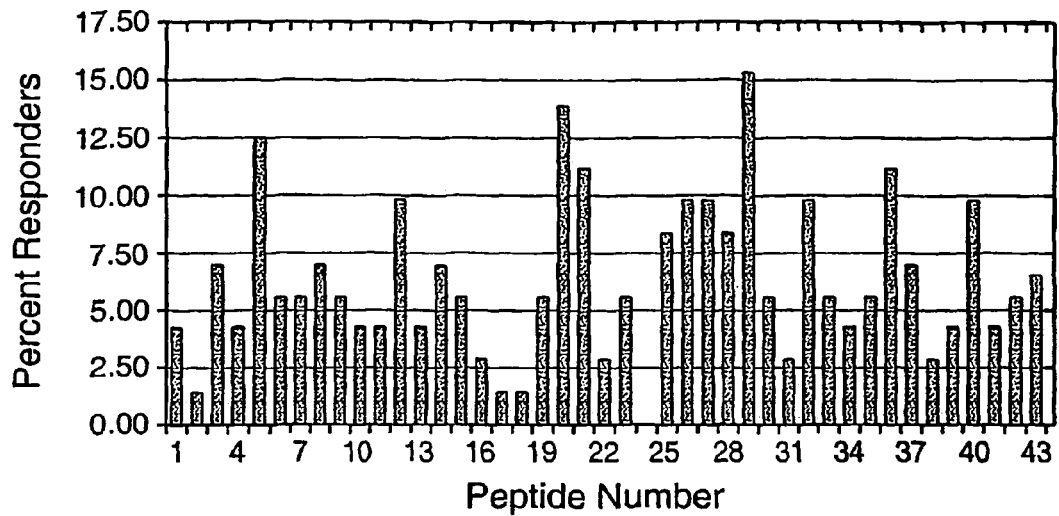
FIG._14A
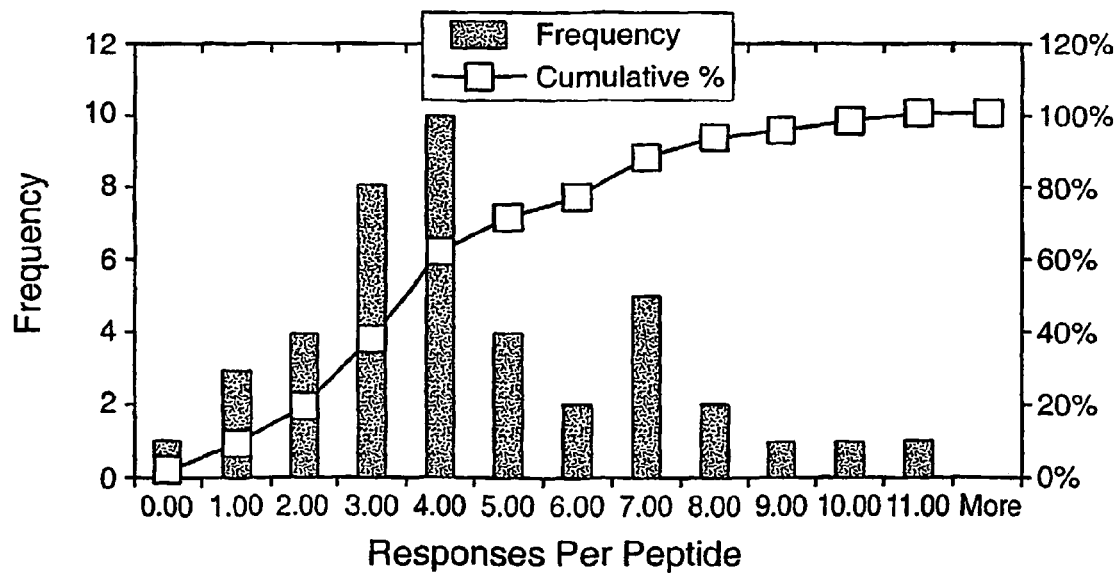
FIG._14B

I-mune® HLA Associations

| Staphylokinase Peptide | HLA Association | p | HLA Increased | HLA Decreased | | Warmerdam, et al (2002)* Region | |
|---|---|---|---|---|---|---|---|
| 5 | | | DQ2 | | 56% vs 27%, p < 0.08 | D1 | DR3, 7, 2 |
| 20 | DR2 (15) | p < 0.03 | DQ6 | | 70% vs 40%, p < 0.08 | F2 | Dr1, 4 |
| | | | | DR7 | 0% vs 23%, p < 0.09 | | |
| 21 | | | DR6 (13) | | 50% vs 23% p < 0.11 | C3 | DR2, 3, 4, 6, 7, 8 |
| 29 | DR5 (11) | p < 0.01 | | | | n.f.# | n.f.# |
| 36 | | | DR3 | | 37% vs 14%, p < 0.09 | D4 | DR3, 6 |
| n.f.# | | | | | | A5 | DR2, 5, 6, 8 |

FIG. 15

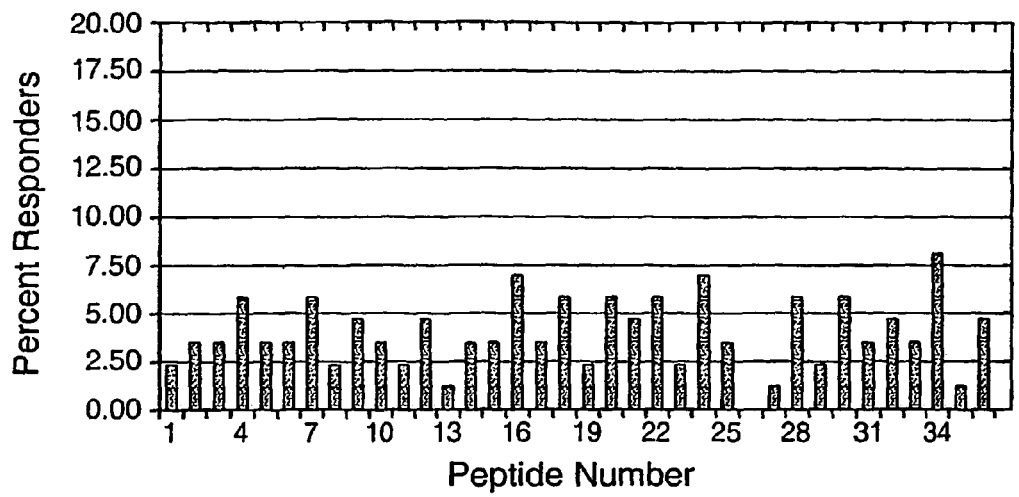
FIG._16A
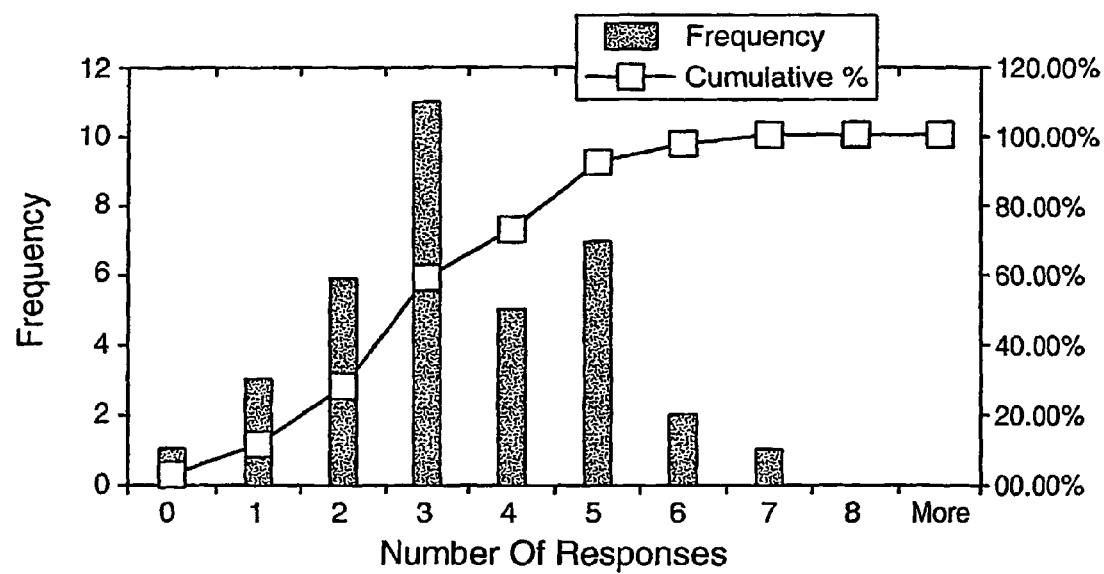
FIG._16B nM IC$_{50}$ For Binding To Purified HLA

| Protein | DRB1 | | | | | | | | | | |
|---|---|---|---|---|---|---|---|---|---|---|---|
| | *0101 (DR1) | *0301 (DR3w17) | *0401 (DR4w4) | *0404 (DR4w14) | *0405 (DR4w15) | *0701 (DR7) | *0802 (DR8w2) | *0901 (DR9) | *1101 (DR5w11) | *1201 (DR5w12) | |
| BPN'Y217L.70 | 6.5 | 8737 | 33 | 5.7 | 166 | 154 | 1711 | 46 | 2382 | 80 | |
| BPN'Y217L.109 | 8.8 | -- | 30 | 166 | 37 | 58 | 2192 | 43 | 3019 | 1235 | |
| B. lentus 157 | 1065 | 16,433 | 4794 | 7575 | 6784 | 724 | >16,333 | 1484 | -- | -- | |
| B. lentus 160 | 13 | -- | 142 | 5542 | 1348 | 138 | 2033 | 164 | 5554 | -- | |

| DRB1 | | DRB3/4/5 | | | DQ | | | Degeneracy |
|---|---|---|---|---|---|---|---|---|
| *1302 (DR6w19) | *1501 (DR2w2β1) | *DRB3*0101 (DR52a) | *DRB4*0101 (DRw53) | *DRB5*0101 (DR2w2β2) | DQA1*0501/ DQB1*0201 (DQ2) | DQA1*0301/ DQB1*0301 (DQ3.1) | DQA1*0301/ DQB1*0302 (DQ3.2) | n/18 |
| 0.69 | 21 | 2010 | 31 | 15,689 | 670 | 440 | 2069 | 12 |
| 9.8 | 683 | 119 | 1071 | 1024 | 97 | 2182 | 80 | 11 |
| 2009 | 865 | >9434 | >9667 | -- | 6157 | 6009 | 5009 | 2 |
| 559 | 127 | 6157 | 8257 | 1726 | 1296 | 63 | 1046 | 7 |

FIG._17

POPULATION BASED ASSESSMENTS AND MEANS TO RANK THE RELATIVE IMMUNOGENICITY OF PROTEINS

FIELD OF THE INVENTION

The present invention provides means to assess immune response profiles of populations. In particular, the present invention provides means to qualitatively assess the immune response of human populations, wherein the immune response directed against any protein of interest is analyzed. The present invention further provides means to rank proteins based on their relative immunogenicity. In addition, the present invention provides means to create proteins with reduced immunogenicity for use in various applications.

BACKGROUND OF THE INVENTION

Proteins have the capacity to induce potentially life-threatening immune responses. This limitation has hindered their widespread use in consumer end-use applications and products. Indeed, this potential to induce immune responses has come to the attention of the U.S. Food and Drug Administration (FDA), resulting in the requirement for immunogenicity testing both prior to and after approval of new protein therapeutics. However, although there are a number of animal models available for assessing immunogenicity, there are no validated methods to discern relative immunogenicity in humans.

Despite these concerns, the immunogenicity of proteins has long been a concern in the enzyme manufacturing industry. Occupational exposure to proteins has been documented to result in sensitization of industrial and laboratory workers. Sensitization to particular proteins is usually assessed by tests such as the skin-prick test that reveals whether an individual has mounted an immune response to the protein.

Indeed, occupational exposure to proteins has been documented to result in sensitization of industrial and laboratory workers. In most settings, sensitization is controlled by reducing the level of airborne protein (See, Sarlo and Kirchner, Curr. Opin. Allergy Clin. Immunol., 2:97-101 [2002]; and Schweigert et al., Clin. Exp. Allergy 30:1511-1518 [2000]). Occupational exposure guidelines have been implemented that control airborne exposure to proteins. These guidelines, which provide the allowable level of exposure to particular proteins have been useful in reducing the overall number of sensitization events occurring in a given industrial setting. When a new protein is to be manufactured, the establishment of occupational exposure guidelines (OEGs) for the new protein is a matter of serious concern. A commonly accepted method to determine these guidelines is the guinea pig intra-tracheal test (GPIT) (See, Sarlo, Fundam. Appl. Toxicol., 39:44-52 [1997]). In this test, guinea pigs are exposed to the test protein via intra-tracheal instillation for a period of about 10-12 weeks. Serum samples from the animals are taken periodically and tested for their levels of antigen-specific antibody by suitable methods known in the art (e.g., passive cutaneous testing (PCA) for $IgG_1$ and by micro-immunodiffusion testing (MID) for precipitating IgG). These results are compared to results obtained from a set of guinea pigs tested with control proteins that have known, effective exposure guidelines (e.g., ALCALASE® enzyme, commercially available from Novo). Determination of serum titers, MID positivity and time to response are considered, and a relative potency value is determined. This method has been used successfully to set OEGs for a number of industrial enzymes.

However, while the GPIT test is useful, it is time consuming and expensive, requiring a number of animals and multiple rounds of testing. Relatively recently, a mouse-based test was established that is reported to reproduce the results obtained in the GPIT, through the use of a less expensive and less cumbersome animal model. The mouse intranasal test (MINT; See, Robinson et al., Toxicol. Sci. 43:39-46 [1998]) is used by some companies to set OEG guidelines. However, industry-wide acceptance has not been achieved for this model (for reviews of predictive tests for protein allergenicity, see Robinson et al., supra, as well as Kimber et al., (Kimber et al., Fundam. Appl. Toxicol., 33:1-10 [1996]; and Kimber et al., Toxicol. Sci., 48:157-162 [1999]).

Thus, although animal models are useful, they have limitations. The use of partially outbred guinea pigs in the GPIT necessitates the use of large numbers of animals in order to achieve statistical significance when comparing responses between groups. In addition, inter-experiment variation in control animal responses is very high, which makes potency determinations based on a single set of control responses less convincing. The MINT assay does not suffer from as much variability in antibody responses because the mice used are typically BDF1 mice, a cross between two highly inbred mouse strains. While this additional level of control allows for more robust data analyses, different strains of mice typically return very different potency rankings for similar enzymes (See, Blaikie, Food Chem. Toxicol., 37:897-904 [1999]; and Blaikie and Basketter, Food Chem. Toxicol., 37:889-896 [1999]). This is likely due to the specificity of the immune response in a mouse line that is been inbred to express very limited MHC molecules. In addition, while data from an individual lab using the MINT assay may be robust, the MINT assay is also plagued by inter-laboratory differences.

Significantly, all animal tests suffer from the inability to provide a suitable representation of the immune response to a given protein in humans. Inbred strains of mice present peptide molecules with the specificity conferred by their murine MHC molecules. Human HLA molecules, while highly related to mouse MHC molecules, do not have identical peptide specificities. Furthermore, inbred mouse strains have been selected for expression of a single I-A and/or I-E molecule, a situation that very rarely occurs in the highly outbred human population. In addition, the mouse immune system has a number of properties which are not found in humans (e.g., the Th1 versus Th2 paradigm that has been described in mice is much less clear in humans). For example, in humans, there is plasticity in Th1 and Th2 phenotypes that can be explained by a genetic inconsistency in the IFN-alpha gene. In contrast, in mice, the Th1 and Th2 phenotypes are not dynamic, due to an insertion in the IFN-alpha gene in these animals (See, Farrar, Nat. Immunol., 1:65-69 [2000]). In addition, humans express HLA class II molecules on activated T cells, while mice do not. Furthermore, human donors typically carry endogenous viruses, and often have subclinical infections, while laboratory mice are typically maintained in a specific-pathogen free (SPF) environment. Another concern is that the C57Bl/6 mouse strain, a popular background for the creation of transgenic mouse models, carries a defined antigen-processing defect that makes comparisons to human derived data of questionable reliability (Kim and Jang, Eur. J. Immunol., 22:775-782 [1992]). Human HLA transgenic mice have become available for application to the mechanistic study of human immune responses (See, Boyton and Altmann, Clin. Exp. Immunol., 127:4-11 [2002]; Black et al., J. Immunol., 169:5595-5600 [2002]; Raju et al., Hum. Immunol., 63:237-247 [2002]; and Das et al., Rev. Immunogenet., 2:105-114 [2000]). However, the use of these animals is limited, as HLA transgenic mice suffer from species-specific immune system complexities. In addition, at least some of the methods used to construct these mice do not allow for accurate analysis of peptide-specific responses, as expression of the HLA transgenes is not correctly regulated. HLA transgenic mice are often used for mapping studies when expressing a single HLA molecule, a situation not found in humans. This is especially of note for HLA-DQ transgenic mice where cross-pairing between different HLA-DQ alleles has been shown to create new peptide presentation specificities (See, Krco et al., J. Immunol., 163:1661-1665 [1999]). Thus, despite advances in the determination, assessment, and comparisons of the immunogenicity of proteins, there remains a need in the art for simple, reliable and reproducible methods to make such determinations.

Likewise, the application of proteins to therapeutic, industrial and nutritional uses is limited by the potential for inducing or exacerbating deleterious immune responses. This potential is especially of concern for the use of recombinant human-derived proteins. Indeed, recombinant human-derived proteins have been demonstrated to induce immune responses directed at self-proteins, resulting in the development of autoimmunity (Li et al., Blood 98:3241-3248 [2001]; and Casadell et al., N. Eng. J. Med., 346:469-475 [2002]). Subsequent reactivation of the immune system after unintended induction of immune responses to industrial or food proteins can be minimized by avoidance. However, this is not the case with human-derived therapeutic proteins. The selection and/or creation of reduced immunogenic protein variants is therefore necessary to improve safety and efficacy of administered proteins. The selection of a naturally occurring hypo-immunogenic protein isomer is an option where several related molecules with similar activities exist. Unfortunately, this is not an option for many therapeutic proteins. Thus, there is a long-felt need in the art for means to produce hypo-immunogenic proteins suitable for use as therapeutics and for other applications.

SUMMARY OF THE INVENTION

The present invention provides means to assess immune response profiles of populations. In particular, the present invention provides means to qualitatively assess the immune response of human populations, wherein the immune response directed against any protein of interest is analyzed. The present invention further provides means to rank proteins based on their relative immunogenicity. In addition, the present invention provides means to create proteins with reduced immunogenicity for use in various applications.

The present invention was developed In order to avoid the issues arising from immunogenicity analyses in animals other than humans. In preferred embodiments of the present invention, means are provided to rank the immunogenicity of proteins using human peripheral blood monocytes (PBMC) as the test "subject." Because large replicates of human samples are used, the information provided is applicable to general populations of humans. Importantly, the data do not suffer from the specificity issues surrounding the use of inbred mice. In preferred embodiments, the present invention provides means to rank proteins based on their overall immunogenicity. In addition, by comparing data with pre-existing animal data, the methods of the present invention provide information pertaining to the relative potency of proteins. For example, during the development of the present invention, four well-characterized industrial allergens were placed in the order determined by the GPIT and MINT tests, and were compared with the results obtained using the methods of the present invention, including determining the sensitization of occupationally exposed workers.

In preferred embodiments, the methods provided by the present invention involve the use of dendritic cells as antigen-presenting cells, 15-mer peptides offset by 3 amino acids that encompass an entire protein sequence of interest, and $CD4^+$ T-cells obtained from the dendritic cell donors. T-cells are allowed to proliferate in a sample in the presence of the peptides (each peptide is tested individually) and differentiated dendritic cells. It is not intended that any of the methods of the present invention be conducted in any particular order, as far as preparation of pepsets and differentiation of dendritic cells. For example, in some embodiments, the pepsets are prepared before the dendritic cells are differentiated, while in other embodiments, the dendritic cells are differentiated before the pepsets are prepared, and in still other embodiments, the dendritic cells are differentiated and the pepsets are prepared concurrently. Thus, it is not intended that the present invention be limited to methods having these steps in any particular order.

If the proliferation in response to a peptide results in a stimulation index (SI) of 1.5 to 4.5, the response is considered and tallied as being "positive." The results for each peptide are tabulated for a donor set, which preferably reflects the general HLA allele frequencies of the population, albeit with some variation. The "structure value," based on the determination of difference from linearity is determined, and this value is used to rank the relative immunogenicity of the proteins. Thus, the present invention provides information useful in the modification of proteins, such that reduced response rates predicted to be effective in humans are achieved without the need to sensitize volunteers. Analyses of donor responses to peptide sets based on these new proteins that have been designed to be hypoimmunogenic are then conducted to calculate structure values for the new protein(s) and confirm their immunogenicity and exposure potentials.

In some preferred embodiments, the invention provides an assay system (i.e., the I-MUNE® assay) for ranking relative immunogenicity of proteins. In one embodiment, the methods comprise measuring in vitro $CD4^+$ T-cell proliferation in response to peptide fragments of a protein, compiling the measured responses for the protein, determining the structure value of the compiled responses, and comparing the structure value of the protein to the structure value of a second protein, wherein the protein comprising the lowest structure value is ranked as being less immunogenic to a human compared to a protein having a higher structure value. In alternative embodiments, the tested protein is an enzyme. In still further embodiments, the enzyme is a protease. In an additional embodiment, the tested protein is selected from the group consisting of antibodies, cytokines, and hormones. In a further embodiment, the T-cell proliferation of each peptide fragment and each protein is determined in side-by-side tests. In other embodiments, a "positive" response is determined based on an SI value between 2.7 and 3.2. In particularly preferred embodiments, the level of proliferation results in a stimulation index of 2.95 or greater.

The present invention also provides methods for assessing the reduced immunogenic capacity of variant proteins in humans. In some embodiments, the methods comprise reducing one or more prominent regions of a parent protein to a background level to create a variant protein, determining the structure value of the variant, and comparing the structure value of the variant with the structure value of the parent protein, wherein the lower structure value indicates a protein with reduced immunogenicity. In some preferred embodiments, the protein is an enzyme. In some alternative embodiments, the protein is selected from the group consisting of proteases, cytokines, hormones, antibodies, amylases, and other enzymes, including but not limited to subtilisins, ALCALASE® enzyme, cellulases, lipases, oxidases, isomerases, kinases, phosphatases, lactamases, and reductases. In further embodiments, the number of prominent regions reduced to background level are between 1 and 10, preferably between 1 and 5. In yet another embodiment, one or more amino acid residues are altered in the prominent region of the parent protein to create a variant.

The present invention also provides methods for selecting the least immunogenic protein from a group of related proteins. In one embodiment, the related proteins are antibodies, while in an alternative embodiment they are cytokines, and in yet another embodiment, they are hormones. In a further embodiment, the related proteins are structural proteins. In yet another embodiment, the proteins are enzymes. In some preferred embodiments, the enzymes are selected from the group consisting of proteases, cellulases, lipases, amylases, oxidases, isomerases, kinases, phosphatases, lactamases, and reductases.

The present invention further provides methods of using the relative ranking of related proteins to determine T-cell epitope modification suitable to reduce the immunogenicity of the proteins, particularly in humans. The present invention also provides means to categorize proteins based on both their background percent response and their structure values. Thus, in some further embodiments, the proteins analyzed are categorized and/or ranked according to their background percent response and structure values.

In some embodiments, the present invention provides methods for ranking the relative immunogenicity of a first protein and at least one additional protein, comprising the steps of: (a) preparing a first pepset from a first protein and preparing at least one additional pepset from each of the additional proteins, wherein each of the pepsets (b) obtaining from a single human blood source a solution comprising dendritic cells and a solution of naïve CD4+ and/or CD8+ T-cells; (c) differentiating the dendritic cells to produce a solution of differentiated dendritic cells; (d) combining the solution of differentiated dendritic cells and the naïve CD4+ and/or CD8+ T-cells with the first pepset; (e) combining the solution of differentiated dendritic cells and the naïve CD4+ and/or CD8+ T-cells with each of the pepsets from the additional proteins; measuring proliferation of the T-cells in steps (d) and (e), to determine the responses to each peptide in the first and additional pepsets; (g) compiling the responses of the T-cells in step (f) for the first protein and the additional proteins; (h) determining the structure value of the compiled responses of step (g) for the first protein and the additional proteins; and (i) comparing the structure value obtained for the first protein with the structure value for the additional proteins to determine the immunogenicity ranking of the first protein and the additional proteins. In some preferred embodiments, the pepsets comprise peptides of about 15 amino acids in length, while in some particularly preferred embodiments each peptide overlaps adjacent peptides by about 3 amino acids. However, it is not intended that the peptides within the pepsets be limited to any particular length nor overlap, as other peptide lengths and overlap amounts find use in the present invention.

In some embodiments, the protein having the lowest structure value is ranked as being less immunogenic than the protein having the higher structure value. In additional embodiments, the at least two proteins are selected from the group consisting of enzymes, hormones, cytokines, antibodies, structural proteins, and binding proteins. In still further embodiments, a positive response against the first protein comprises a stimulation index value between about 2.7 and about 3.2. In yet other embodiments, a positive response against the additional proteins comprises a stimulation index value between about 2.7 and about 3.2. In further embodiments, a positive response against the first protein comprises a stimulation index value between about 2.7 and about 3.2 and a positive response against the additional proteins comprises a stimulation index value between about 2.7 and about 3.2. In some embodiments, proliferation of the T-cells in steps (d) results in a stimulation index of about 2.95 or greater, while in additional embodiments, the proliferation of the T-cells in steps (e) results in a stimulation index of about 2.95 or greater. In still further embodiments, the proliferation of the T-cells in steps (d) results in a stimulation index of about 2.95 or greater and the proliferation of the T-cells in steps (e) results in a stimulation index of about 2.95 or greater. In some particularly preferred embodiments, at least one additional human blood source is used in step (b). In some additional particularly preferred embodiments, the structure values obtained for each of the human blood sources and the proteins are compared. The present invention also provides means to categorize proteins based on both their background percent response and their structure values. Thus, in some further embodiments, the proteins analyzed are categorized and/or ranked according to their background percent response and structure values.

The present invention also provides methods for ranking the relative immunogenicity of two proteins, wherein the second protein is a protein variant of the first protein, comprising the steps of: (a) preparing a first pepset from a first protein and a second pepset from a second protein; (b) obtaining from a single human blood source a solution comprising dendritic cells and a solution of naïve CD4+ and/or CD8+ T-cells; (c) differentiating the dendritic cells to produce a solution of differentiated dendritic cells; (d) combining the solution of differentiated dendritic cells and the naïve CD4+ and/or CD8+ T-cells with the first pepset; (e) combining the solution of differentiated dendritic cells and the naïve CD4+ and/or CD8+ T-cells with the second pepset; (f) measuring proliferation of the T-cells in steps (d) and (e), to determine the responses to each peptide in the first and second pepsets; (g) compiling the responses of the T-cells in step (f) for the first protein and the second protein; (h) determining the structure value of the compiled responses of step (g) for the first protein and the second protein; (i) comparing the structure value obtained for the first protein with the structure value for the second protein to determine the immunogenicity ranking of the first protein and the second protein. In some embodiments, the second protein is ranked as less immunogenic than the first protein, while in alternative embodiments, the first protein is ranked as less immunogenic than the second protein. In some preferred embodiments, the pepsets comprise peptides of about 15 amino acids in length, while in some particularly preferred embodiments each peptide overlaps adjacent peptides by about 3 amino acids. However, it is not intended that the peptides within the pepsets be limited to any particular length nor overlap, as other peptide lengths and overlap amounts find use in the present invention. In additional embodiments, the first and second proteins are selected from the group consisting of enzymes, hormones, cytokines, antibodies, structural proteins, and binding proteins. In still further embodiments, a positive response against the first protein comprises a stimulation index value between about 2.7 and about 3.2, while in other embodiments, a positive response against the second protein comprises a stimulation index value between about 2.7 and about 3.2. In additional embodiments, a positive response against the first protein comprises a stimulation index value between about 2.7 and about 3.2 and a positive response against the second protein comprises a stimulation index value between about 2.7 and about 3.2. In still further embodiments, the proliferation of the T-cells in steps (d) results in a stimulation index of about 2.95 or greater and the proliferation of the T-cells in steps (e) results in a stimulation index of about 2.95 or greater. In some particularly preferred embodiments, at least one additional human blood source is used in step (b). In some additional particularly preferred embodiments, the structure values obtained for each of the human blood sources and the proteins are compared. In some embodiments, the second protein comprises a reduction of at least one prominent region in the first protein. In further embodiments, the proliferation of the T-cells in step (e) is at a background level. In some particularly preferred embodiments, the structure values obtained for each of the human blood sources and the proteins are compared. The present invention also provides means to categorize proteins based on both their background percent response and their structure values. Thus, in some further embodiments, the proteins analyzed are categorized and/or ranked according to their background percent response and structure values.

The present invention also provides methods for ranking the relative immunogenicity of a first protein and at least one variant protein, comprising the steps of: (a) preparing a first pepset from a first protein and pepsets from each of the variant proteins; (b) obtaining from a single human blood source a solution comprising dendritic cells and a solution of naïve CD4+ and/or CD8+ T-cells; (c) differentiating the dendritic cells to produce a solution of differentiated dendritic cells; (d) combining the solution of differentiated dendritic cells and the naïve CD4+ and/or CD8+ T-cells with the first pepset; (e) combining the solution of differentiated dendritic cells and the naïve CD4+ and/or CD8+T-cells with each pepset prepared from each of the variant proteins; (f) measuring proliferation of the T-cells in steps (d) and (e), to determine the responses to each peptide in the first and second pepsets; (g) compiling the responses of the T-cells in step (f) for the first protein and the variant protein(s); (h) determining the structure value of the compiled responses of step (g) for the first protein and the variant protein(s); and (i) comparing the structure value obtained for the first protein with the structure value for the variant protein(s) to determine the immunogenicity ranking of the first protein and the variant proteins. In some preferred embodiments, the pepsets comprise peptides of about 15 amino acids in length, while in some particularly preferred embodiments each peptide overlaps adjacent peptides by about 3 amino acids. However, it is not intended that the peptides within the pepsets be limited to any particular length nor overlap, as other peptide lengths and overlap amounts find use in the present invention. In some preferred embodiments, at least one of the variant proteins is ranked as less immunogenic than the first protein, while in other embodiments, the first protein is ranked as less immunogenic than at least one of the variant proteins. In additional embodiments, first and the variant proteins are selected from the group consisting of enzymes, hormones, cytokines, antibodies, structural proteins, and binding proteins. In further embodiments, a positive response against the first protein comprises a stimulation index value between about 2.7 and about 3.2, while in other embodiments, a positive response against a variant protein comprises a stimulation index value between about 2.7 and about 3.2. In additional embodiments, a positive response against the first protein comprises a stimulation index value between about 2.7 and about 3.2 and a positive response against a variant protein comprises a stimulation index value between about 2.7 and about 3.2. In still further embodiments, the proliferation of the T-cells in steps (d) results in a stimulation index of about 2.95 or greater and the proliferation of the T-cells in steps (e) results in a stimulation index of about 2.95 or greater. In some particularly preferred embodiments, at least one additional human blood source is used in step (b). In some additional particularly preferred embodiments, the structure values obtained for each of the human blood sources and the proteins are compared. In some embodiments, the variant protein comprises a reduction of at least one prominent region in the first protein. In further embodiments, the proliferation of the T-cells in step (e) is at a background level. In some preferred embodiments, the proliferation of the T-cells in step (e) for at least one variant protein is at a background level. In some particularly preferred embodiments, the structure values obtained for each of the human blood sources and the proteins are compared. In further embodiments, at least one additional human blood source is used in step (b). The present invention also provides means to categorize proteins based on both their background percent response and their structure values. Thus, in some further embodiments, the proteins analyzed are categorized and/or ranked according to their background percent response and structure values.

The present invention further provides methods for determining the immune response of a test population against a test protein, comprising the steps of: (a) preparing a pepset from a test protein; (b) obtaining a plurality of solutions comprising human dendritic cells and a plurality of solutions of naïve human CD4+ and/or CD8+ T-cells, wherein the solutions of human dendritic cells and solutions of naïve human CD4+ and/or CD8+ T-cells are obtained from a plurality of individuals within the test population; (c) differentiating the dendritic cells to produce a plurality of solutions comprising differentiated dendritic cells; (d) combining the plurality of the solutions of differentiated dendritic cells and the solutions of naïve CD4+ and/or CD8+ T-cells with the pepset, wherein each of the solutions of differentiated dendritic cells and the solutions of naïve CD4+ and/or CD8+ T-cells are from one individual within the test population are combined; (e) measuring proliferation of the T-cells in step (d), to determine the responses to each peptide in the pepset; (g) compiling the responses of the T-cells in step (e) for the test protein; (h) determining the structure value of the compiled responses of step (g) for the test protein; and (i) determining the level of exposure of the plurality of individuals to the test protein. In some preferred embodiments, the pepsets comprise peptides of about 15 amino acids in length, while in some particularly preferred embodiments each peptide overlaps adjacent peptides by about 3 amino acids. However, it is not intended that the peptides within the pepsets be limited to any particular length nor overlap, as other peptide lengths and overlap amounts find use in the present invention. In some embodiments, at least two test proteins are tested. In some preferred embodiments, the level of exposure of the plurality of individuals to the test protein is compared. In some particularly preferred embodiments, the test protein is modified to produce a variant protein that exhibits a reduced immunogenic response in the test population. The present invention also provides means to categorize proteins based on both their background percent response and their structure values. Thus, in some further embodiments, the proteins analyzed are categorized and/or ranked according to their background percent response and structure values.

BRIEF DESCRIPTION OF THE FIGURES

FIG. 1 illustrates the average frequency of the HLA-DRB1 allele for 184 random individuals in the community donor population compared to published "Caucasian" HLA-DRB1 populations.

FIG. 2 illustrates the percent of responders from a population of 82 random individuals tested with peptides derived from Bacillus licheniformis alpha amylase. The consecutive 15-mer peptides offset by 3 amino acids are listed on the x-axis and the percentages of donors who responded to each peptide are shown on the y-axis.

FIG. 3 illustrates the percent of responders from a population of 65 random individuals tested with peptides derived from Bacillus lentus subtilisin. The consecutive 15-mer peptides offset by 3 amino acids are listed on the x-axis and the percent of donors who responded to each peptide is shown on the y-axis.

FIG. 4 illustrates the percent responders from a population of 113 individuals tested with two peptide sets from a Bacillus BPN' subtilisin Y217L. The consecutive 15-mer peptides offset by 3 amino acids are listed on the x-axis and the percentage of donors who responded to each peptide are shown on the y-axis.

FIG. 5 illustrates the percent responders from a population of 92 individuals tested with peptides derived from ALCALASE® enzyme. The consecutive 15-mer peptides offset by 3 amino acids are listed on the x-axis and the percentages of donors who responded to each peptide are shown on the y-axis.

FIG. 6 provides a graph showing that the calculated structure values decrease with increasing number of responses per peptide. The structure values shown were those determined for α-amylase (squares) and BPN' Y217L (diamonds), as responses accumulated.

FIG. 7, Panels A and B provide a comparison between GPIT (Panel A) and MINT (Panel B) ranking data and the structure index values for four industrial enzymes. The relative allergenicities of α-amylase, ALCALASE® enzyme, BPN' Y217L, and B. lentus subtilisin as determined in guinea pig (GPIT) and mouse (MINT)-based assays are compared to the structure index values (y-axis).

FIG. 8 provides a graph showing a limited dataset indicating the variant peptide responses used to calculate the structure for the BPN' Y217L variant. Forty-eight community donors were tested with peptides derived from the sequence of BPN' Y217L. The consecutive 15-mer peptides offset by 3 amino acids are listed on the x-axis and the percentages of the donors who responded to each peptide are shown on the y-axis. The last two peptides represent variant sequences of peptides number 24 and 37.

FIG. 9 provides a graph showing the maximum proliferative responses of PBMC from 30 community donors to BPN' Y217L (open triangles, structure value=0.53) and the unmodified BPN' Y217L variant (closed squares, structure value=0.40). Each donor's maximum response is shown on the y-axis. An SI of 2.0 was the cut-off for a "positive" response. The difference in proliferative responses between BPN' Y217L and the variant was p<0.01.

FIG. 10 provides a graph showing the relative structure value and background percent of responses to the 25 proteins tested as described in Example 5.

FIG. 11 provides a graph showing the average percent response per peptide for each of 11 tested proteins for the donors tested.

FIG. 12, provides graphs showing the frequency of responses to B. lentus subtilisin (n=65 community donors). Panel A show the percent of responses to linear peptides describing the sequence of subtilisin. The consecutive peptides are shown on the x-axis. Percent response within the 65 donors is on the y-axis. Panel B shows the frequency of responses within the set. The frequency of responses to the peptides within the B. lentus peptide set is shown.

FIG. 13 provides a graph showing the responses of seven SPT+ (skin prick test positive) donors to B. lentus peptides. PBMC from 7 donors verified to be sensitized to B. lentus subtilisin by skin prick test were used in the I-MUNE® assay of the present invention to test for their responses to B. lentus subtilisin peptides. A response to a peptide was considered positive if an SI of 2.95 or greater was observed. The number of donors responding to each peptide is shown on the y-axis. The consecutive B. lentus peptides are shown on the x-axis.

FIG. 14 provides graphs showing I-MUNE® assay data results for staphylokinase. Panel A provides the percent responders per peptide (n=72). The consecutive staphylokinase peptides are shown on the x-axis. The percent responders within the donor set of 72 is shown on the y-axis. Panel shows the frequency of responses per peptide.

FIG. 15 provide a table showing the epitope alignment between the I-MUNE® assay results obtained using the I-MUNE® assay system of the present invention and published epitopes for staphylokinase.

FIG. 16 provides graphs showing the I-MUNE® assay results for β2-microglobulin. Panel A shows the percent responders per peptide (n=87). The consecutive human β2-microglobulin peptides are shown on the x-axis. The percent response within the 87 donor set is shown on the y-axis. Panel B shows the frequency of responses per peptide.

FIG. 17 provides a table showing the $IC_{50}$ binding values for epitope peptides identified in bacterial proteases by the I-MUNE® assay system of the present invention. Values less than 500 nM are considered to be good binders and are highlighted in bold in the Table. Degeneracy indicates the number of HLA class II proteins that bind with an $IC_{50}$ of less than 500 nM out of the 18 total alleles tested.

DESCRIPTION OF THE INVENTION

The present invention provides means to assess immune response profiles of populations. In particular, the present invention provides means to qualitatively assess the immune response of human populations, wherein the immune response directed against any protein of interest is analyzed. The present invention further provides means to rank proteins based on their relative immunogenicity. In addition, the present invention provides means to create proteins with reduced immunogenicity for use in various applications.

The present invention provides ex vivo techniques for the identification of CD4+ T-cell epitopes on a human population basis. Within a donor population pre-sensitized to the protein of interest, all recall epitopes can be defined. For a donor population defined as un-sensitized to the protein of interest, either primary or cross-reactive epitopes are identified. While the latter cannot be formally ruled out, a number of points support the conclusion that the epitopes found are primary epitopes. First, the epitopes found in industrial proteins are largely promiscuous binders with low $IC_{50}$ values in an in vitro binding assay. Recall responses are marked by lower threshold values over time rather than being narrowed to the highest binding values (See, Hesse et al., J. Immunol., 167: 1353-1361 [2001]). Second, a subset of total recall epitopes is always found when using presumably unsensitized donors. This is a characteristic of primary, immunodominant epitopes (See, Muraro et al., J. Immunol., 164:5474-5481 [2000]; Vanderlugt, Nat. Rev. Immunol., 2:85-95 [2002]; Vanderlugt, J. Immunol., 164:670-678 [2000]; and Yin et al., J. Immunol., 26:2063-2068 [1998]). Third, β-2 microglobulin was tested as a set of 15-mer peptides off-set by 3 amino acids, representing a group of 52 peptides to which no prominent epitope responses were found. It seems unlikely that none of these sequences would be found to be cross-reactive sequences in any other proteins. Four, when a epitope cross-reactive with a sequence found in a protein from a human pathogenic agent is found, as was the case for one bacterial enzyme protein examined, the percent responses to the epitope peptide were very high (30%), much higher than any responses collated in the other 10 industrial enzymes tested as described in Example 7 (data not shown). Five, the I-MUNE® assay system of the present invention is performed using CD4+ T cell enriched responders cells and activated monocyte-derived dendritic cells as APCs. The magnitude of proliferative responses seen is very small, consistent with a low precursor frequency of antigen-specific CD4+ T cells. Recall proliferative responses were detected as being much more robust than the responses detected in the presumably un-sensitized population. Finally, BLAST searches were performed with the epitope sequences. For the *Bacillus*-derived proteins, *Bacillus* species contain protease variants that have modifications within the epitope sequences identified. However, it is unlikely that the donor pool would become sensitized to these, or any of the other *Bacillus* serine proteases (with the notable cross-reactive example cited above). Interestingly, there is some homology (66% homology) of the amino acids 70-84 epitope region in BPN' Y217L to a region in a putative human-derived ATP-dependent RNA helicase (See, Imamura et al., Nucl. Acids Res., 26:2063-2068 [1998]). Homology to a widely expressed housekeeping gene such as this might be expected to induce tolerance rather than provoke a cross-reactive response.

The background rate is an important consideration in analyzing population data. The background rate is contributed to by both accumulating positive responses at epitope peptides, as well as random events that reach the 2.95 SI cut-off value. The low level of randomly accumulating positive responses reflects the heterogeneity of the proliferation status of CD4+ T cells in human donors (See, Asquith et al., Trends Immunol., 23:595-601 [2002]). While the background could be reduced artificially by raising the cutoff response value, having a measurable rate of background allows for the determination of where the frequency of responses accumulate in a non-random manner. For example, the background response rate to HPV16 E6 was significantly higher than the rate for industrial enzymes, likely reflecting the high prevalence of HPV16 infection in the community donor population (Lazcano-Ponce et al., Int'l J. Cancer 91:412-420 [2001]; and Stone et. al., J. Infect. Dis., 186:1396-1402 [2002]). The same situation is likely for staphylokinase.

In spite of all the variables included in the I-MUNE® assay system, the coefficient of variance (CV) for the frequency of epitope responses was very good (an average of 20% for four tested peptides). This level of reproducibility compares favorably to coefficient of variable values reported for intra-laboratory and inter-donor repeat testing of primary ELISPOT data, an analogous ex vivo assay (Keilhoz et al., J. Immunother., 25:97-138 [2002]; and Asai et al., Clin. Diag. Lab Immunol., 7:145-154 [2000]). Generally, CV values decline as the percent response to an epitope peptide increases. In addition, non-epitope peptide responses with reduced frequencies (usually less than 10% of the donor population) have increased CV values. For example, in Example 7, the overall background rate was 3.15% with a standard deviation of 1.6%, a CV of 51%.

The statistical method for defining epitope peptides is different if the population demonstrates presentitization to the protein of interest. An increased background response is likely due to the reduced threshold for functional activation seen in recall responses (See, Hesse et al., supra). Reduced thresholds for functional activation result in more epitopes being detected by the I-MUNE® assay system of the present invention. A comparison of the I-MUNE® assay system results with data from sensitized donors showed that the prominent epitope responses in the I-MUNE® assay data aligned with epitope responses defined by clonal CD4+ T cell lines. By reducing the level of stringency of the statistical method, the selection of epitope peptides within the I-MUNE® assay system corresponded with the published epitope sequences. The designation of epitope status in datasets with very low background rates, such as the industrial enzyme data, was more stringent. When the background responses are very low, many peptides accumulate responses that meet the cut-off value if the reduced stringency determination is used, but the overall frequency of responses is very low, and will be difficult to reproduce. Typically, when responses are less than 10% of the total population they become difficult to reproduce due to the technical difficulty of testing more than 100 donors. Significant epitope responses are easily deduced from the frequency data, where epitope responses are outliers. Epitope peptide sequences in unsensitized donors likely reflect tight binding promiscuous epitopes capable of inducing de-novo proliferation (Viola and Lanzavecchi, Science 273:104-106 [1996]; and Rachmilewitz and Lanzavecchia, Trends Immunol., 23:592-595 [2002]). This was confirmed for epitope peptides designated in two industrial enzymes by in vitro peptide binding studies (See, Example 7).

The I-MUNE® assay system of the present invention did not identify any epitopes in human β2-microglobulin. This result highlights the difference between the I-MUNE® assay system of the present invention and algorithm-based HLA class II binding prediction methods. Peptide-binding algorithms freely available via the internet and known to those in the art, predict class II binding epitopes in this sequence. However, as exemplified by the results presented here, binding to a class II molecule does not always indicate the presence of a functional epitope. Binding to HLA class II is necessary, but not sufficient, to define T cell epitopes. This is a well-known property of predictive methods, and therefore these methods are often supplemented with functional testing. However, the present invention provides a more direct means to obtain this information.

It is important to note that the epitope determinations described herein are defined on a population basis. While prominent epitopes often show some level of HLA specificity, the epitope peptides are largely defined by their promiscuous HLA binding capacity. Because of this, these epitopes are likely supertype binders and therefore represent good candidates for modification, if a hypo-immunogenic protein is sought. However, it is contemplated that due to the population based analysis, hypo-immunogenic proteins created using these results as a guide are not always non-immunogenic in every discrete instance. Nonetheless, defining T-cell epitopes on a population basis finds use in characterization of immune responses to infectious agents (See, Novitsky et al., J. Virol., 76:10155-10168 [2002]; and Pathan et al., J. Immunol., 167: 5217-5225 [2001]). One purpose for such studies is to design efficacious vaccines, where the inclusion of promiscuous supertype binders is also warranted. Interestingly, when the data presented in one of these studies (Pathan et al., supra) was subjected to analysis by the exposed-donor method defined herein, the same set of dominant epitope responses were selected (data not shown).

In addition to its utility in the infectious disease setting, as well as protein analyses, the methods of the present invention provide means to localize the functional CD4+ T cell epitopes in any protein of interest. When the donor population is expected to be un-exposed to the protein of interest, the background response rate is low, and stringent statistics can be applied to the selection of CD4+ epitope sequences. Interestingly, human proteins have very low background responses. A high background level corresponds with donor exposure to the protein of interest, and the epitope determination relies on less stringent criteria. Epitope designations have been validated by comparison to results for verified sensitized donors. As indicated above, no epitopes were found in human β-2 microglobulin, as would be expected for a ubiquitously expressed protein that imprints tolerance on the immune system. Thus, the present I-MUNE® assay system provides a valuable tool for predicting population-based CD4+ T-cell epitopes. The applications for this technology include the creation of hypo-immunogenic protein variants, the selection of epitope regions for the creation of epitope-based vaccines, and as a tool for inclusion in the risk assessment evaluation of all commercial proteins.

Indeed, the present invention provides means to reduce the sensitization potential of CD4+ T-cells. This is particularly of use in target populations that have not been previously exposed to a potential commercial protein or any other protein intended for use by/for humans and other animals. Indeed, in addition to the creation of hypo-allergenic/immunogenic commercial protein variants, T-cell epitope identification is the basis of many vaccine strategies (Alexander et al., Immunol. Res., 18:79-2 [1998]; and Berzofsky, Ann. N.Y. Acad. Sci., 690:256-264 [1993]). The identification of T cell epitopes recognized by individuals who clear pathogens versus those who do not is of interest to the design of both cancer and viral vaccines (Manici et al., J. Exp. Med., 189:871-87 [1999]; Doolan et al., J. Immunol., 165:1123-1137; and Novitsky et al., J. Virol., 76:10155-10168 [2002]). The utility of hypo-allergenic/immunogenic proteins is also clear for personal care, health care, and home care settings, as well as in commercial applications. Indeed, such hypo-allergenic/immunogenic proteins find use in innumerable settings and uses.

For the creation of CD4+ T cell epitope-modified proteins, the first critical step is the localization of functional epitopes within the protein. There are a number of computer-based methods for predicting the localization of peptide sequences that bind to HLA class II molecules (Yu et al., Mol. Med., 8:137-148 [2002]; Rammensee et al., Immunogenet., 50:213-219 [1990]; Sturniolo et al., Nat. Biotechnol., 17:555-561 [1999]; and Altuvia et al., J. Mol. Biol., 249:244-250 [1995]). Binding to HLA is necessary, but not sufficient, for CD4+ T cell activation. Optimally, in vitro and in vivo testing must be performed to confirm functionality. Computer based methods are improving in their ability to correctly identify tight HLA binders, but still suffer from a lack of prediction for binding non HLA-DR class II molecules, and a significant false negative rate. In addition, functional differences such as the induction of tolerance, and epitopes that induce differential responses by activated T cells cannot be assessed using computer modeling.

Thus, the present invention provides means heretofore unavailable for the identification and confirmation of functionality of methods for assessing CD4+ T-cell epitope-modified proteins. In some embodiments, the present invention provides in vitro human cell based method for the localization of immunodominant, promiscuous HLA class II epitopes from any protein of interest. The method applies equally well to industrial enzymes, food allergens, and human therapeutic proteins as it does to the delineation of population-based epitope responses to pathogen-derived proteins, as well as any other protein of interest. In preferred embodiments, large donor sets are tested without pre-selection for HLA type. Epitope determinations are made based on statistical analyses of the response rates by the entire donor set to all the peptides derived from the sequence of the protein, and therefore represent population-based epitopes. As indicated herein, the methods of the present invention are capable of distinguishing between proteins to which the donor population has been exposed, from proteins that the donor population has not previously encountered or has not become sensitized to. During the development of the present invention, both types of analyses were compared to proliferation results from verified antigen-sensitized donors. In addition, human β2-microglobulin was tested and confirmed as a negative control.

As referred to herein, epitope peptides are designated by difference from the background response rate. Epitope peptide responses are reproducible, with a median coefficient of variance of 21% when tested on multiple random-donor sets. In addition, as discussed in greater detail herein, the I-MUNE® assay system of the present invention identified recall epitopes for the protein staphylokinase, and identified immunodominant promiscuous epitopes in industrial proteases representing a subset of the total recall epitopes. Furthermore, the I-MUNE® assay system found no epitopes in the negative control (i.e., human β-2 microglobulin). Importantly, the present invention provides means to identify functional CD4+ T cell epitopes in any protein without pre-selection for HLA class II type, suggesting whether a donor population is pre-exposed to a protein of interest, and does not require sensitized donors for in vitro testing.

During the development of the present invention, the use of statistical analysis of peptide-specific responses in a large human donor pool provided a metric that ranked four industrial enzymes in the order determined by both mouse and guinea pig exposure models. The ranking method also compared favorably to human sensitization rates in occupationally exposed workers. Additional confirmation of the methods of the present invention were also determined, based on structure values for proteins known to cause sensitization in humans. Comparison of these results indicated that the sensitization levels were found to be higher than the value determined for human β2-microglobulin. In preferred embodiments, the present invention provides comparative methods to predict the immunogenicity of various related and unrelated proteins in humans. Thus, the information provided by the present invention finds use in the early development of protein therapies and other protein-based applications to select or create reduced immunogenicity variants.

DEFINITIONS

Unless defined otherwise herein, all technical and scientific terms used herein have the same meaning as commonly understood by one of ordinary skill in the art to which this invention pertains. For example, Singleton and Sainsbury, *Dictionary of Microbiology and Molecular Biology,* 2d Ed., John Wiley and Sons, New York (1994); and Hale and Marham, *The Harper Collins Dictionary of Biology*, Harper Perennial, New York (1991) provide those of skill in the art with a general dictionaries of many of the terms used in herein. Although any methods and materials similar or equivalent to those described herein find use in the practice of the present invention, the preferred methods and materials are described herein. Accordingly, the terms defined immediately below are more fully described by reference to the Specification as a whole.

As used herein, the term "population" refers to the individuals associated with, and/or residing, in a given area. In some embodiments, the term is used in reference to a number of individuals that share a common characteristic (e.g., the population with a particular HLA type, etc.). Although the term is used in reference to human populations in preferred embodiments, it is not intended that the term be limited to humans, as it finds use in reference to other animals and organisms. In some embodiments, the term is used in in reference to the total set of items, characteristics, individuals, etc., from which a sample is taken.

As used herein, the term "population-based immune response" refers to the immune response profiles (i.e., characteristics) of the members of a population.

As used herein, the term "immune response" refers to the immunological response mounted by an organism (e.g., a human or other animal) against an immunogen. It is intended that the term encompass all types of immune responses, including but not limited to humoral (i.e., antibody-mediated), cellular, and non-specific immune responses. In some embodiments, the term reflects the immunity levels of populations (i.e., the number of people who are "immune" to a particular antigen and/or the number of people who are "not immune" to a particular antigen).

As used herein, the term "reduced immunogenicity" refers to a reduction in the immune response that is observed with variant (e.g., derivative) proteins, as compared to the original wild-type (e.g. parental or source) protein. In preferred embodiments of the present invention, variant proteins that stimulate a less robust immune response in vitro and/or in vivo, as compared to the source protein are provided. It is contemplated that these proteins having reduced immunogenicity will find use in various applications, including but not limited to bioproducts, protein therapeutics, food and feed, personal care, detergents, and other consumer-associated products, as well as in other treatment regimens, diagnostics, etc.

As used herein, the term "enhanced immunogenicity" refers to an increase in the immune response that is observed with variant (e.g., derivative) proteins, as compared to the original wild-type (e.g. parental or source) protein. In preferred embodiments of the present invention, variant proteins that stimulate a more robust immune response in vitro and/or in vivo, as compared to the source protein are provided. It is contemplated that these proteins having enhanced immunogenicity will find use in various applications, including but not limited to bioproducts, protein therapeutics, food and feed additives, as well as in other treatment regimens, diagnostics, etc.

As used herein, "allergenic food protein" refers to any food protein that is associated with causing an allergic reaction in humans and other animals. A "putative allergenic food protein" is a food protein that may be allergenic. A "food protein with reduced allergenicity" is a food protein that has been modified so as to be less allergenic (i.e., "hypoallergenic") than the original, unmodified protein. It is intended that these terms encompass naturally-occurring food proteins, as well as those produced synthetically and/or using recombinant technology.

As used herein "altered immunogenic response," refers to an increased or reduced immunogenic response. Proteins and peptides exhibit an "increased immunogenic response" when the T-cell and/or B-cell response they evoke is greater than that evoked by a parental (e.g., precursor) protein or peptide (e.g., the protein of interest). The net result of this higher response is an increased antibody response directed against the variant protein or peptide. Proteins and peptides exhibit a "reduced immunogenic response" when the T-cell and/or B-cell response they evoke is less than that evoked by a parental (e.g., precursor) protein or peptide. The net result of this lower response is a reduced antibody response directed against the variant protein or peptide. In some preferred embodiments, the parental protein is a wild-type protein or peptide.

As used herein, "Stimulation Index" (SI) refers to a measure of the T-cell proliferative response of a peptide compared to a control. The SI is calculated by dividing the average CPM (counts per minute) obtained in testing the $CD4^+$ T-cell and dendritic cell culture containing a peptide by the average CPM of the control culture containing dendritic cells and $CD4^+$ T-cells but without the peptides. This value is calculated for each donor and for each peptide. While in some embodiments, SI values of between about 1.5 to 4.5 are used to indicate a positive response, the preferred SI value to indicate a positive response is between 2.5 and 3.5, inclusive, preferably between 2.7 and 3.2 inclusive, and more preferably between 2.9 and 3.1 inclusive. The most preferred embodiments described herein use a SI value of 2.95.

As used herein, the term "dataset" refers to compiled data for a set of peptides and a set of donors for tested for their responses against each test protein (i.e., a protein of interest).

As used herein, the term "pepset" refers to the set of peptides produced for each test protein (i.e., protein of interest). These peptides in the pepset (or "peptide sets") are tested with cells from each donor.

As used herein, the terms "Structure" and "Structure Value" refer to a value to rank the relative immunogenicity of proteins. The structure value is determined according to the "total variation distance to the uniform" formula below:

$$\sum\left|f(i)-\frac{1}{p}\right|$$

wherein:

Σ (upper case sigma) is the sum of the absolute value of the frequency of responses to each peptide minus the frequency of that peptide in the set; f(i) is defined as the frequency of responses for an individual peptide; and ρ is the number of peptides in the peptide set. In preferred embodiments of the present invention, a structure value is determined for each protein tested. Based on the structure values obtained, the test proteins are ranked from the lowest value to the highest value in the series of tested proteins. In this ranked series, the lowest value indicates the least immunogenic protein, while the highest value indicates the most immunogenic protein.

The structure value is dependent on the number of donors (i.e., the number of blood samples obtained from different individuals) tested. In general, zero responses across the entire dataset provide a structure value of 1.0. The same number of responses at each peptide returns a structure value of zero. Therefore, in preferred embodiments, a peptide set should be tested until there are responses across the majority of the dataset, in order for the data to accurately reflect responsivity to particular peptides and peptide regions. In particularly preferred embodiments, there is a response to every peptide in the dataset. However, some datasets do not exhibit responses to every peptide in the dataset due to various factors (e.g., insolubility issues).

While the above formula is the preferred formula to use for determination of the structure value, other equivalent formulas find use in the present invention. For example, the "entropy of the distribution" formula finds use in the present invention, as well as various other formulae known to those in the art.

In some embodiments, the peptide sets are tested with at least as many donors as should produce a response per peptide given the overall rate of 3% non-specific responses. For example, in preferred embodiments, a peptide set of 88 peptides is tested with a minimum of 30 donors. Thus, in embodiments in which the pepset includes more peptides, the number of donors is adjusted accordingly. Nonetheless, 30 donors is the preferred minimum number. Of course, more donors may be tested using the methods of the present invention, even when fewer peptides are present within a pepset. In some preferred embodiments, the dataset includes at least 50 donors, in order to provide good HLA allele representation.

As used herein, a "prominent response" refers to a peptide that produces an in vitro T-cell response rate in the dataset that is greater than about 2.0-fold the background response rate. In a further embodiment, the response is about a 2.0-fold to about a 5.0-fold increase above the background response rate. Also included within this term are responses that represent about a 2.5 to 3.5-fold increase, about a 2.8 to 3.2-fold increase, and a 2.9 to 3.1-fold increase above the background response rate. For example, during the development of the present invention, prominent responses were noted for some of the peptides.

As used herein, "prominent region" refers to an I-MUNE® assay response obtained with a particular peptide set that is greater than about 2.0-fold the background response rate. In one embodiment of the present invention, all of the prominent regions of a protein are reduced so that their responses in the I-MUNE® assay system of the present invention are reduced. In further embodiments, the number of prominent regions are reduced by 1, 2, 3, 4, 5, 6, 7, 8, 9, 10 or more, and preferably between 1 and 5 prominent regions are reduced in related proteins. In some embodiments, prominent regions also meet the requirements for a T-cell epitope.

The term "sample" as used herein is used in its broadest sense. However, in preferred embodiments, the term is used in reference to a sample (e.g., an aliquot) that comprises a peptide (e.g., a peptide within a pepset, that comprises a sequence of a protein of interest) that is being analyzed, identified, modified, and/or compared with other peptides. Thus, in most cases, this term is used in reference to material that includes a protein or peptide that is of interest.

As used herein, "background level" and "background response" refer to the average percent of responders to any given peptide in the dataset for any tested protein. This value is determined by averaging the percent responders for all peptides in the set, as compiled for all the tested donors. As an example, a 3% background response would indicate that on average there would be three positive (Si greater than 2.95) responses for any peptide in a dataset when tested on 100 donors.

As used herein, "antigen presenting cell" ("APC") refers to a cell of the immune system that presents antigen on its surface, such that the antigen is recognizable by receptors on the surface of T-cells. Antigen presenting cells include, but are not limited to dendritic cells, interdigitating cells, activated B-cells and macrophages.

As used herein, the terms "T lymphocyte" and "T-cell," encompass any cell within the T lymphocyte lineage from T-cell precursors (including Thy1 positive cells which have not rearranged the T cell receptor genes) to mature T cells (i.e., single positive for either CD4 or CD8, surface TCR positive cells).

As used herein, the terms "B lymphocyte" and "B-cell" encompasses any cell within the B-cell lineage from B-cell precursors, such as pre-B-cells ($B220^+$ cells which have begun to rearrange Ig heavy chain genes), to mature B-cells and plasma cells.

As used herein, "$CD4^+$ T-cell" and "CD4 T-cell" refer to helper T-cells, while "$CD8^+$ T-cell" and CD8 T-cell" refer to cytotoxic T-cells.

As used herein, "B-cell proliferation," refers to the number of B-cells produced during the incubation of B-cells with the antigen presenting cells, with or without the presence of antigen.

As used herein, "baseline B-cell proliferation," as used herein, refers to the degree of B-cell proliferation that is normally seen in an individual in response to exposure to antigen presenting cells in the absence of peptide or protein antigen. For the purposes herein, the baseline B-cell proliferation level is determined on a per sample basis for each individual as the proliferation of B-cells in the absence of antigen.

As used herein, "B-cell epitope," refers to a feature of a peptide or protein which is recognized by a B-cell receptor in the immunogenic response to the peptide comprising that antigen (i.e., the immunogen).

As used herein, "altered B-cell epitope," refers to an epitope amino acid sequence which differs from the precursor peptide or peptide of interest, such that the variant peptide of interest produces different (i.e., altered) immunogenic responses in a human or another animal. It is contemplated that an altered immunogenic response encompasses altered immunogenicity and/or allergenicity (i.e., an either increased or decreased overall immunogenic response). In some embodiments, the altered B-cell epitope comprises substitution and/or deletion of an amino acid selected from those residues within the identified epitope. In alternative embodiments, the altered B-cell epitope comprises an addition of one or more residues within the epitope.

"T-cell proliferation," as used herein, refers to the number of T-cells produced during the incubation of T-cells with the antigen presenting cells, with or without the presence of antigen.

"Baseline T-cell proliferation," as used herein, refers to the degree of T-cell proliferation that is normally seen in an individual in response to exposure to antigen presenting cells in the absence of peptide or protein antigen. For the purposes herein, the baseline T-cell proliferation level is determined on a per sample basis for each individual as the proliferation of T-cells in response to antigen presenting cells in the absence of antigen.

As used herein, "T-cell epitope" refers to a feature of a peptide or protein which is recognized by a T-cell receptor in the initiation of an immunogenic response to the peptide comprising that antigen (i.e., the immunogen). Although it is not intended that the present invention be limited to any particular mechanism, it is generally believed that recognition of a T-cell epitope by a T-cell is via a mechanism wherein T-cells recognize peptide fragments of antigens which are bound to Class I or Class II MHC (i.e., HLA) molecules expressed on antigen-presenting cells (See e.g., Moeller, Immunol. Rev., 98:187 [1987]).

As used herein, "altered T-cell epitope," refers to an epitope amino acid sequence which differs from the precursor peptide or peptide of interest, such that the variant peptide of interest produces different immunogenic responses in a human or another animal. It is contemplated that an altered immunogenic response encompasses altered immunogenicity and/or allergenicity (i.e., an either increased or decreased overall immunogenic response). In some embodiments, the altered T-cell epitope comprises substitution and/or deletion of an amino acid selected from those residues within the identified epitope. In alternative embodiments, the altered T-cell epitope comprises an addition of one or more residues within the epitope.

As used herein, "protein of interest," refers to a protein (e.g., protease) which is being analyzed, identified and/or modified. Naturally-occurring, as well as recombinant proteins find use in the present invention. Indeed, the present invention finds use with any protein against which it is desired to characterize and/or modulate the immunogenic response of humans (or other animals). In some embodiments, proteins including hormones, cytokines, antibodies, enzymes, structural proteins and binding proteins find use in the present invention. In some embodiments, hormones, including but not limited to insulin, erythropoietin (EPO), thromopoietin (TPO) and luteinizing hormone (LH) find use in the present invention. In further embodiments, cytokines including but not limited to interferons (e.g., IFN-alpha and IFN-beta), interleukins (e.g., IL-1 through IL-15), tumor necrosis factors (e.g., TNF-alpha and TNF-beta), and GM-CSF find use in the present invention. In yet other embodiments, antibodies (i.e., immunoglobulins), including but not limited to human and humanized antibodies, antibody-derived fragments (e.g., single chain antibodies) of any class, find use in the present invention. In still other embodiments, structural proteins including but not limited to food allergens (e.g., Ber e 1 [Brazil nut allergen] and Ara H 1 [peanut allergen]) find use in the present invention. In additional embodiments, the proteins are industrial and/or medicinal enzymes. In some embodiments, preferred classes of enzymes include, but are not limited to proteases, cellulases, lipases, esterases, amylases, phenol oxidases, oxidases, permeases, pullulanases, isomerases, kinases, phosphatases, lactamases and reductases.

As used herein, "protein" refers to any composition comprised of amino acids and recognized as a protein by those of skill in the art. The terms "protein," "peptide" and polypeptide are used interchangeably herein. Wherein a peptide is a portion of a protein, those skill in the art understand the use of the term in context. The term "protein" encompasses mature forms of proteins, as well as the pro- and prepro-forms of related proteins. Prepro forms of proteins comprise the mature form of the protein having a prosequence operably linked to the amino terminus of the protein, and a "pre-" or "signal" sequence operably linked to the amino terminus of the prosequence.

As used herein, "wild-type" and "native" proteins are those found in nature. The terms "wild-type sequence," and "wild-type gene" are used interchangeably herein, to refer to a sequence that is native or naturally occurring in a host cell. In some embodiments, the wild-type sequence refers to a sequence of interest that is the starting point of a protein engineering project.

As used herein, "protease" refers to naturally-occurring proteases, as well as recombinant proteases. Proteases are carbonyl hydrolases which generally act to cleave peptide bonds of proteins or peptides. Naturally-occurring proteases include, but are not limited to such examples as α-aminoacylpeptide hydrolase, peptidylamino acid hydrolase, acylamino hydrolase, serine carboxypeptidase, metallocarboxypeptidase, thiol proteinase, carboxylproteinase and metalloproteinase. Serine, metallo, thiol and acid proteases are included, as well as endo and exo-proteases. Indeed, in some preferred embodiments, serine proteases such as chymotrypsin and subtilisin find use. Both of these serine proteases have a catalytic triad comprising aspartate, histidine and serine. In the subtilisin proteases, the relative order of these amino acids reading from the carboxy terminus is aspartate-histidine-serine, while in the chymotrypsin proteases, the relative order of these amino acids reading from the carboxy terminus is histidine-asparate-serine. Although subtilisins are typically obtained from bacterial, fungal or yeast sources, "subtilisin" as used herein, refers to a serine protease having the catalytic triad of the subtilisin proteases defined above. Additionally, human subtilisins are proteins of human origin having subtilisin catalytic activity, for example the kexin family of human derived proteases. Subtilisins are well known by those skilled in the art for example, Bacillus amyloliquefaciens subtilisin (BPN'), Bacillus lentus subtilisin, Bacillus subtilis subtilisin, Bacillus licheniformis subtilisin (See e.g., U.S. Pat. No. 4,760,025 (RE 34,606), U.S. Pat. No. 5,204,015, U.S. Pat. No. 5,185,258, EP 0 328 299, and WO89/06279).

As used herein, functionally similar proteins are considered to be "related proteins." In some embodiments, these proteins are derived from a different genus and/or species (e.g., B. subtilis subtilisin and B. lentus subtilisin), including differences between classes of organisms (e.g., a bacterial subtilisin and a fungal subtilisin). In additional embodiments, related proteins are provided from the same species. Indeed, it is not intended that the present invention be limited to related proteins from any source(s).

As used herein, the term "derivative" refers to a protein (e.g., a protease) which is derived from a precursor protein (e.g., the native protease) by addition of one or more amino acids to either or both the C- and N-terminal end(s), substitution of one or more amino acids at one or a number of different sites in the amino acid sequence, and/or deletion of one or more amino acids at either or both ends of the protein or at one or more sites in the amino acid sequence, and/or insertion of one or more amino acids at one or more sites in the amino acid sequence. The preparation of a protease derivative is preferably achieved by modifying a DNA sequence which encodes for the native protein, transformation of that DNA sequence into a suitable host, and expression of the modified DNA sequence to form the derivative protease.

One type of related (and derivative) proteins are "variant proteins." In preferred embodiments, variant proteins differ from a parent protein and one another by a small number of amino acid residues. The number of differing amino acid residues may be one or more, preferably 1, 2, 3, 4, 5, 10, 15, 20, 30, 40, 50, or more amino acid residues. In one preferred embodiment, the number of different amino acids between variants is between 1 and 10. In particularly preferred embodiments, related proteins and particularly variant proteins comprise at least 50%, 60%, 65%. 70%, 75%, 80%, 85%, 90%, 95%, 97%, 98%, or 99% amino acid sequence identity. Additionally, a related protein or a variant protein as used herein, refers to a protein that differs from another related protein or a parent protein in the number of prominent regions. For example, in some embodiments, variant proteins have 1, 2, 3, 4, 5, or 10 corresponding prominent regions which differ from the parent protein. In one embodiment, the prominent corresponding region of a variant produces only a background level of immunogenic response.

As used herein, "corresponding to," refers to a residue at the enumerated position in a protein or peptide, or a residue that is analogous, homologous, or equivalent to an enumerated residue in another protein or peptide.

As used herein, "corresponding region" generally refers to an analogous position within related proteins or a parent protein.

As used herein, the term "analogous sequence" refers to a sequence within a protein that provides similar function, tertiary structure, and/or conserved residues as the protein of interest. In particularly preferred embodiments, the analogous sequence involves sequence(s) at or near an epitope. For example, in epitope regions that contain an alpha helix or a beta sheet structure, the replacement amino acids in the analogous sequence preferably maintain the same specific structure.

As used herein, "homologous protein" refers to a protein (e.g., protease) that has similar catalytic action, structure, antigenic, and/or immunogenic response as the protein (e.g., protease) of interest. It is not intended that a homolog and a protein (e.g., protease) of interest be necessarily related evolutionarily. Thus, it is intended that the term encompass the same functional protein obtained from different species. In some preferred embodiments, it is desirable to identify a homolog that has a tertiary and/or primary structure similar to the protein of interest, as replacement for the epitope in the protein of interest with an analogous segment from the homolog will reduce the disruptiveness of the change. Thus, in most cases, closely homologous proteins provide the most desirable sources of epitope substitutions. Alternatively, it is advantageous to look to human analogs for a given protein.

As used herein, “homologous genes” refers to at least a pair of genes from different, but usually related species, which correspond to each other and which are identical or very similar to each other. The term encompasses genes that are separated by speciation (i.e., the development of new species) (e.g., orthologous genes), as well as genes that have been separated by genetic duplication (e.g., paralogous genes).

As used herein, “ortholog” and “orthologous genes” refer to genes in different species that have evolved from a common ancestral gene (i.e., a homologous gene) by speciation. Typically, orthologs retain the same function in during the course of evolution. Identification of orthologs finds use in the reliable prediction of gene function in newly sequenced genomes.

As used herein, “paralog” and “paralogous genes” refer to genes that are related by duplication within a genome. While orthologs retain the same function through the course of evolution, paralogs evolve new functions, even though some functions are often related to the original one. Examples of paralogous genes include, but are not limited to genes encoding trypsin, chymotrypsin, elastase, and thrombin, which are all serine proteinases and occur together within the same species.

The degree of homology between sequences may be determined using any suitable method known in the art (See e.g., Smith and Waterman, Adv. Appl. Math., 2:482 [1981]; Needleman and Wunsch, J. Mol. Biol., 48:443 [1970]; Pearson and Lipman, Proc. Natl. Acad. Sci. USA 85:2444 [1988]; programs such as GAP, BESTFIT, FASTA, and TFASTA in the Wisconsin Genetics Software Package (Genetics Computer Group, Madison, Wis.); and Devereux et. al., Nucl. Acid Res., 12:387-395 [1984]).

For example, PILEUP is a useful program to determine sequence homology levels. PILEUP creates a multiple sequence alignment from a group of related sequences using progressive, pairwise alignments. It can also plot a tree showing the clustering relationships used to create the alignment. PILEUP uses a simplification of the progressive alignment method of Feng and Doolittle, (Feng and Doolittle, J. Mol. Evol., 35:351-360 [1987]). The method is similar to that described by Higgins and Sharp (Higgins and Sharp, CABIOS 5:151-153 [1989]). Useful PILEUP parameters including a default gap weight of 3.00, a default gap length weight of 0.10, and weighted end gaps. Another example of a useful algorithm is the BLAST algorithm, described by Altschul et al., (Altschul et al., J. Mol. Biol., 215:403-410, [1990]; and Karlin et al., Proc. Natl. Acad. Sci. USA 90:5873-5787 [1993]). One particularly useful BLAST program is the WU-BLAST-2 program (See, Altschul et al., Meth. Enzymol., 266:460-480 [1996]). parameters “W,” “T,” and “X” determine the sensitivity and speed of the alignment. The BLAST program uses as defaults a wordlength (W) of 11, the BLOSUM62 scoring matrix (See, Henikoff and Henikoff, Proc. Natl. Acad. Sci. USA 89:10915 [1989]) alignments (B) of 50, expectation (E) of 10, M'5, N'-4, and a comparison of both strands.

As used herein, “percent (%) nucleic acid sequence identity” is defined as the percentage of nucleotide residues in a candidate sequence that are identical with the nucleotide residues of the sequence.

As used herein, the term “hybridization” refers to the process by which a strand of nucleic acid joins with a complementary strand through base pairing, as known in the art.

As used herein, “maximum stringency” refers to the level of hybridization that typically occurs at about Tm-5° C. (5° C. below the Tm of the probe); “high stringency” at about 5° C. to 10° C. below Tm; “intermediate stringency” at about 10° C. to 20° C. below Tm; and “low stringency” at about 20° C. to 25° C. below Tm. As will be understood by those of skill in the art, a maximum stringency hybridization can be used to identify or detect identical polynucleotide sequences while an intermediate or low stringency hybridization can be used to identify or detect polynucleotide sequence homologs.

In some embodiments, “equivalent residues” are defined by determining homology at the level of tertiary structure for a precursor protein (i.e., protein of interest) whose tertiary structure has been determined by x-ray crystallography. Equivalent residues are defined as those for which the atomic coordinates of two or more of the main chain atoms of a particular amino acid residue of the precursor protein and another protein are within 0.13 nm and preferably 0.1 nm after alignment. Alignment is achieved after the best model has been oriented and positioned to give the maximum overlap of atomic coordinates of non-hydrogen protein atoms of the protein. In most embodiments, the best model is the crystallographic model giving the lowest R factor for experimental diffraction data at the highest resolution available.

In some embodiments, modification is preferably made to the “precursor DNA sequence” which encodes the amino acid sequence of the precursor enzyme, but in alternative embodiments, it is made by the manipulation of the precursor protein. In the case of residues which are not conserved, the replacement of one or more amino acids is limited to substitutions which produce a variant which has an amino acid sequence that does not correspond to one found in nature. In the case of conserved residues, such replacements should not result in a naturally-occurring sequence. Derivatives provided by the present invention further include chemical modification(s) that change the characteristics of the protease.

In some preferred embodiments, the protein gene is ligated into an appropriate expression plasmid. The cloned protein gene is then used to transform or transfect a host cell in order to express the protein gene. This plasmid may replicate in hosts in the sense that it contains the well-known elements necessary for plasmid replication or the plasmid may be designed to integrate into the host chromosome. The necessary elements are provided for efficient gene expression (e.g., a promoter operably linked to the gene of interest). In some embodiments, these necessary elements are supplied as the gene's own homologous promoter if it is recognized, (i.e., transcribed by the host), a transcription terminator (a polyadenylation region for eukaryotic host cells) which is exogenous or is supplied by the endogenous terminator region of the protein gene. In some embodiments, a selection gene such as an antibiotic resistance gene that enables continuous cultural maintenance of plasmid-infected host cells by growth in antimicrobial-containing media is also included.

In embodiments involving proteases, variant protease activity is determined and compared with the protease of interest by examining the interaction of the protease with various commercial substrates, including, but not limited to casein, keratin, elastin, and collagen. Indeed, it is contemplated that protease activity will be determined by any suitable method known in the art. Exemplary assays to determine protease activity include, but are not limited to, succinyl-Ala-Ala-Pro-Phe-para nitroanilide (SAAPFpNA) (citation) assay; and 2,4,6-trinitrobenzene sulfonate sodium salt (TNBS) assay. In the SAAPFpNA assay, proteases cleave the bond between the peptide and p-nitroaniline to give a visible yellow color absorbing at 405 nm. In the TNBS color reaction method, the assay measures the enzymatic hydrolysis of the substrate into polypeptides containing free amino groups. These amino groups react with TNBS to form a yellow colored complex. Thus, the more deeply colored the reaction, the more activity is measured. The yellow color can be determined by various analyzers or spectrophotometers known in the art.

Other characteristics of the variant proteases can be determined by methods known to those skilled in the art. Exemplary characteristics include, but are not limited to thermal stability, alkaline stability, and stability of the particular protease in various substrate or buffer solutions or product formulations.

When combined with the enzyme stability assay procedures disclosed herein, mutants obtained by random mutagenesis can be identified which demonstrated either increased or decreased alkaline or thermal stability while maintaining enzymatic activity.

Alkaline stability can be measured either by known procedures or by the methods described herein. A substantial change in alkaline stability is evidenced by at least about a 5% or greater increase or decrease (in most embodiments, it is preferably an increase) in the half-life of the enzymatic activity of a mutant when compared to the precursor protein.

Thermal stability can be measured either by known procedures or by the methods described herein. A substantial change in thermal stability is evidenced by at least about a 5% or greater increase or decrease (in most embodiments, it is preferably an increase) in the half-life of the catalytic activity of a mutant when exposed to a relatively high temperature and neutral pH as compared to the precursor protein.

Many of the protein variants of the present invention are useful in formulating various compositions for numerous applications, ranging from personal care to industrial production. For example, a number of known compounds are suitable surfactants useful in detergent compositions comprising the protein mutants of the present invention. These include nonionic, anionic, cationic, anionic or zwitterionic detergents (See e.g., U.S. Pat. No. 4,404,128, U.S. Pat. No. 4,261,868, and U.S. Pat. No. 5,204,015). Thus, it is contemplated that proteins characterized and modified as described herein will find use in various detergent applications. Those in the art are familiar with the different formulations which find use as cleaning compositions. In addition to typical cleaning compositions, it is readily understood that the protein variants of the present invention find use in any purpose that native or wild-type proteins are used. Thus, these variants can be used, for example, in bar or liquid soap applications, dishcare formulations, surface cleaning applications, contact lens cleaning solutions and/or products, peptide hydrolysis, waste treatment, textile applications, as fusion-cleavage enzymes in protein production, etc. For example, the variants of the present invention may comprise, in addition to decreased allergenicity, enhanced performance in a detergent composition (as compared to the precursor). Indeed, it is not intended that the variants of the present invention be limited to any particular use. As used herein, "enhanced performance in a detergent" is defined as increasing cleaning of certain enzyme sensitive stains (e.g., grass or blood), as determined by usual evaluation after a standard wash cycle.

In some embodiments, proteins, particularly enzymes, provided by the means of the present invention are can be formulated into known powdered and liquid detergents having pH between 6.5 and 12.0 at levels of about 0.01 to about 5% (preferably 0.1% to 0.5%) by weight. In some embodiments, these detergent cleaning compositions further include other enzymes such as proteases, amylases, cellulases, lipases or endoglycosidases, as well as builders and stabilizers.

The addition of proteins to conventional cleaning compositions does not create any special use limitations. In other words, any temperature and pH suitable for the detergent are also suitable for the present compositions, as long as the pH is within the above range, and the temperature is below the described protein's denaturing temperature. In addition, proteins of the invention find use in cleaning compositions without detergents, again either alone or in combination with builders and stabilizers.

In one embodiment, the present invention provides compositions for the treatment of textiles that includes variant proteins of the present invention. The composition can be used to treat for example silk or wool (See e.g., RE 216,034; EP 134,267; U.S. Pat. No. 4,533,359; and EP 344,259). In some embodiments, these variants are screened for proteolytic activity according to methods well known in the art.

As indicated above, in preferred embodiments, the proteins of the present invention exhibit modified immunogenic responses (e.g., antigenicity and/or immunogenicity) when compared to the native proteins encoded by their precursor DNAs. In some preferred embodiments, the proteins (e.g., proteases) exhibit reduced allergenicity. Those of skill in the art readily recognize that the uses of the proteases of this invention will be determined, in large part, on the immunological properties of the proteins. For example, proteases that exhibit reduced immunogenic responses can be used in cleaning compositions. An effective amount of one or more protease variants described herein find use in compositions useful for cleaning a variety of surfaces in need of proteinaceous stain removal. Such cleaning compositions include detergent compositions for cleaning hard surfaces, detergent compositions for cleaning fabrics, dishwashing compositions, oral cleaning compositions, and denture cleaning compositions.

An effective amount of one or more related and/or variant proteins with reduced allergenicity/immunogenicity, ranked according to the methods of the present invention find use in various compositions that are applied to keratinous materials such as nails and hair, including but not limited to those useful as hair spray compositions, hair shampoo and/or conditioning compositions, compositions applied for the purpose of hair growth regulation, and compositions applied to the hair and scalp for the purpose of treating seborrhea, dermatitis, and/or dandruff.

In additional embodiments, effective amount(s) of one or more protease variant(s) described herein find use in included in compositions suitable for topical application to the skin or hair. These compositions can be in the form of creams, lotions, gels, and the like, and may be formulated as aqueous compositions or may be formulated as emulsions of one or more oil phases in an aqueous continuous phase.

In addition, the related and/or variant proteins with reduced allergenicity/immunogenicity find use in other applications, including pharmaceutical applications, drug delivery applications, and other health care applications.

DETAILED DESCRIPTION OF THE INVENTION

The present invention provides means to assess immune response profiles of populations. In particular, the present invention provides means to qualitatively assess the immune response of human populations, wherein the immune response directed against any protein of interest is analyzed. The present invention further provides means to rank proteins based on their relative immunogenicity. In addition, the present invention provides means to create proteins with reduced immunogenicity for use in various applications.

The present invention provides methods to assess the overall immunogenic potential of any protein by an analysis of the response rate of individual donors to a set of peptides describing the protein of interest. These methods find use in select the least immunogenic isomer of related proteins. In addition, these methods find use in guiding the development of variant proteins with reduced immunogenicity.

In some preferred embodiments, population-based immune response profiles find use in these methods of developing proteins that have reduced immunogenicity. In addition, the present invention provides means to determine whether or not a particular population has been exposed to a protein of interest, as well as the level of the immune responses among the individuals in the population. This determination provides information useful in the development of proteins with altered immunogenicity characteristics that are desired in applications such as bioproducts, food and feed, protein therapeutics, personal care, healthcare products, detergents, and other consumer-associated goods.

The present invention provides novel means to study the immune responses of populations. As indicated herein, potency determinations for applications involving proteins for administration to humans currently utilize non-human animal models. In addition, T-cell epitopes determinations based on algorithms do not provide the needed information that is provided by the application of the present invention. Indeed, the present invention provides means to assess the immune response profiles of individuals, as well as populations, which provides important information for the rational design and development of protein-containing products.

By analyzing the background response and the structure value of proteins, the immunological "history" of any protein of interest can be determined on a population basis. A high background response indicates population pre-exposure (i.e., more than approximately 4% of the population exhibits immune response to the protein tested). A high structure value indicates a potential immunogen for proteins with low background values, and recent, frequent, and "high quality" immune responses when the protein has a high background. In some embodiments, "high quality" immune responses are observed, due to high levels of immunogen, a robust immune response against the immunogen, and/or a response potentiated by a strong adjuvant.

In some embodiments, low structure values with high backgrounds represent fading immune memory responses, infrequent responses in the population, tolerance induction by exogenous antigen, and/or responses to proteins that are highly diverse (i.e., which may also be a product of a "fading" memory response). It is contemplated that common, non-allergenic food proteins are represented in this type of response profile. In addition, proteins with low structure values and low backgrounds represent comparatively non-immunogenic proteins with no memory response in the population and/or proteins that the human population is tolerized against. In some preferred embodiments, proteins with low background levels of exposure are modified so as to be made "hypoallergenic" (i.e., they do not induce an immune response or induce a lower response, upon exposure to a human or other animal).

To establish a background value for proteins not encountered by the general donor population, the I-MUNE® assay was performed on 11 industrial enzymes including proteases, amylases, laccases, and chitinases (See, Mathies, Tenside Surf. Det., 34:450-454 [1997]). One of the proteases was tested twice using peptides produced in two different formats (PepSet versus purified peptides from Mimotopes). The number of donors tested per peptide set varied from 19 to 113. The number of peptides in each peptide set varied from 80 to 188. A response was tabulated when the stimulation index (S.I. or SI) for an individual peptide was 2.95 or greater. The percent of donors in the tested donor set responding to each peptide was calculated. The average percent response per peptide for each tested protein was calculated, and is shown graphed versus the number of donors tested (See, FIG. 11). The correlation coefficient was $R^2$=0.86. The slope of the correlation reveals the average accumulation rate of responses as 3.01%. Therefore, for any given donor tested with peptides derived from industrial proteins, an average of three peptides out of 100 will return a positive (SI≧2.95) response. This average response rate includes both epitope peptides (see below) and the non-epitope peptides.

Background responses were also calculated by averaging the percent response per peptide in the completed dataset. Averaging the background responses for the 12 tests, the value is 3.15+/−0.45 (average+/− standard error) which is consistent with the value determined by the slope of the correlation trendline.

During the development of the present invention, a group of proteins was selected based on their presumed exposure in the general human population. These proteins included the human papilloma virus (HPV) strain 16 and strain 18 E6 protein, Brazil nut allergen Ber e 1, and staphylokinase. HPV 16 and 18 are the most prevalent forms of tumorigenic HPV viruses. The level of exposure to these viruses has been estimated to be 5 percent or higher for cross-sectional analyses of young women (Lazcano-Ponce et al., Intl. J. Cancer 91:412-420 [2001]; Stone et al., J. Infect. Dis., 186:1396-1402 [2002]; Goldsborough et al., Mol. Cell Probes 6:451-457 [1992]; and Lorincz et al., Obstet. Gynecol., 79:328-337

[1992]). This rate varies with locality and age. Brazil nut allergy occurs in <1% of the population, but exposure to Brazil nuts in food is widespread (Sicherer and Sampson, Curr. Opin. Pediatr., 12:567-573 [2000]). In addition, the rate of staphylokinase-specific T-cell responses in human peripheral blood cell cultures increases with age, with 30% of young donors responding and greater than 70% of donors over age 40 responding (Warmerdam et al., J. Immunol., 168:155-161 [2002]). Peptide sets to these four proteins were tested with samples from local community blood banks. The background responses to all four of these proteins were higher than the average responses found in the 11 industrial enzymes. This is shown as both a higher overall percent background response, and as a higher frequency of responses per peptide as compared to the expected values based on data from the 11 industrial enzymes from FIG. 11. The background responses to HPV 16 E6 and staphylokinase were significantly higher. This result is consistent with the presumed higher exposure rate to these proteins in the donor pool. The background responses to HPV 18 E6 and Ber e 1 were higher than the industrial protein average, but were not significantly different. The increase in background values as compared the industrial protein values is due to the contribution of CD4+ memory responses in the donor population that increase the amplitude, number and complexity of the overall response to a given protein (Kuhns et al., Proc. Natl. Acad. Sci. USA 97:12711-12716 [2000]; Muraro et al., J. Immunol., 164:5474-5481 [2000]; and Vanderlugt and Miller, Nat. Rev. Immunol., 2:85-95 [2002]). Therefore, a higher background rate represents a higher level of sensitization to the tested protein. However, it is not intended that the present invention be limited to any particular mechanism regarding the overall responses against these proteins. For the proteins described herein, it can be concluded that there is significant exposure of our donor population to HPV 16 E6 and staphylokinase, and less exposure to HPV 18 E6 and Ber e 1. The background responses to Ber e 1 and HPV 18 E6 are suggestive of exposure to the proteins, but not at the levels of HPV 16 E6 or staphylokinase.

In addition to these proteins, peptide sets describing human proteins were also tested in during the development of the present invention. These proteins included interferon-β (IFN-β), a cytokine widely expressed during immune responses, thrombopoietin (TPO), a cytokine whose expression is restricted to the bone marrow, and a soluble recombinant cytokine receptor molecule (tumor necrosis factor receptor-1; TNF-R1). Background responses to all four of these proteins were similar to the industrial enzyme background data, suggesting that the donors were responding to the peptides in these sets as if they were unexposed, or "naïve" to these proteins. These data are consistent with the ignorance mechanism of peripheral tolerance to these particular proteins.

In additional embodiments, assessment of the T-cell and/or B-cell epitopes associated with the test proteins is made. In further embodiments, this assessment is utilized in developing rational changes in such epitopes to reduce the immunogenicity/allergenicity of the test proteins (i.e., to produce variant proteins with reduced immunogenicity). These variant proteins then find use in various applications, including but not limited to bioproducts, protein therapeutics, food and feed, personal care, detergents, and other consumer-associated products, as well as in other treatment regimens, diagnostics, etc.

In preferred embodiments, the method uses dendritic cells as antigen-presenting cells, 15-mer peptides offset by 3 amino acids that encompass the entire sequence of the protein, and CD4+ T cells from the dendritic cell donors. A "positive" response is tallied if the average CPM of tritiated thymidine incorporation for a particular peptide is greater than or equal to 2.95 times the background CPM. The results for each peptide are tabulated for a large donor set that should reflect general HLA allele frequencies (with some variations). A statistical calculation based on the determination of "difference from linearity" is performed, and this structure value is used to rank the relative immunogenicity of these proteins. As indicated herein, the ranking results obtained using the methods of the present invention closely reflect immunogenicity determinations (i.e., by the MID assay of Sarlo, [1997], supra) and allergenicity of these proteins as respiratory allergens when determined in occupationally exposed workers (See, Sarlo, supra), or in the GPIT or MINT assay systems (See, Robinson, [1998]) supra).

During the development of the present invention, structure values for a set of proteins including three known immunogens were found to be comparatively high, indicating that these proteins might be capable of inducing immune responses in a significant number of exposed people. Conversely, the structure value for a mouse VH 36-60 gene family member was low, commensurate with its predicted immunogenicity (See, Olsson, J. Theor. Biol., 151:111-122 [1991]). Finally, the structure value determined for β2-microglobulin was low, as would be expected given that this molecule is presumed to be subject to both peripheral and central tolerance mechanisms (See, Guery et al., J. Immunol., 154:545-554 [1995]).

In additional experiments, as described herein, 25 diverse proteins were tested. These data provide a framework for validating the present invention; it is not intended that the present invention be limited to these 25 proteins. Indeed, the present invention finds use in the analysis of any suitable protein of interest in any suitable population of interest. As with the initial experiments described above, the proteins were tested in the I-MUNE® assay system described herein, and structure values were determined. For these 25 proteins, the structure values and background responses delineated four subsets of proteins with varying attributes of interest among the population tested. The ranking method described herein was validated on those proteins with low background responses. Furthermore, all of the proteins tested were compared with those having high background responses. In addition to ranking the potential immunogenicity of the proteins, these embodiments provide information regarding the type of immune response the general population has mounted against the tested proteins.

The comparative immunogenicity of proteins tested in the I-MUNE® assay system of the present invention assume that proteins would be compared in vivo at the same dose, in the same formulation, in a matched set of donors, and over the same dose course. This analysis also precludes any processing and/or presentation differences in the proteins, as well as general physical and structural properties (i.e., stability and activity).

The present invention provides methods that facilitate the localization of T cell epitopes in any protein of interest. For example, in some preferred embodiments, CD4+ T cell epitopes are determined in the absence of individuals sensitized to the test protein. Thus, modification of the peptide epitopes such that reduced response rates predicted to be effective in humans are achievable without the need to sensitize volunteers. In some embodiments, an analysis of donor responses to the modified peptide variants is used to calculate structure values for the new protein. For example, as shown in FIG. 9, a protease variant constructed to have a reduced structure value induced significantly less proliferation in vitro when compared to the parent protein.

The present invention provides distinct advantages in determining the immunogenicity of proteins. In contrast to the present invention, testing of protein variants designed to be less immunogenic by virtue of provoking fewer responses in vitro with large replicates of human donors cannot be rationally tested in guinea pigs or mice. Transgenic mice are limited in their utility, due to the fact that they typically do not express more than one HLA allele, and even then it is often not expressed in a correct context.

Although the ranking of proteins does not imply any fold potency differences, potency differences in guinea pig and mouse models are notoriously inaccurate, susceptible to inter-laboratory as well as inter-experiment variability, and are strain dependent in mice. Indeed, potency determination in animals, particularly guinea pigs is a subjective science, at best. Currently, there is no reliable method to determine potency. However, the present invention provides a means to make potency determinations by extrapolating data based on the alignment of the data determined using the methods of the present method with data obtained from animal experiments. Despite the fact that these potency values are subject to the same inherent inaccuracies as the animal data used to standardize the structure value results, the present invention provides much-improved means to assess immunogenicity, particularly in humans, and determine how best to reduce the immunogenicity of proteins.

Furthermore, the present invention provides means to determine the relative immunogenicity of proteins in human subjects (or other animals) without the necessity of exposing the subjects to the protein of interest. Thus, there is no risk of sensitizing individuals to potentially allergenic/immunogenic substances in order to make the determinations. Importantly, the present invention provides means to rank the immunogenicity of proteins relative to each other, as well as assess the immune response profiles of populations. Indeed, the present invention provides the means to select and/or develop reduced immunogenicity proteins and direct the rational modification of proteins, to create and test hypo-immunogenic variants that are suitable for use in humans and other animals, particularly in humans, Experimental The following examples serve to illustrate certain preferred embodiments and aspects of the present invention and are not to be construed as limiting the scope thereof.

In the experimental disclosure which follows, the following abbreviations apply: eq (equivalents); M (Molar); µM (micromolar); N (Normal); mol (moles); mmol (millimoles); µmol (micromoles); nmol (nanomoles); g (grams); mg (milligrams); kg (kilograms); µg (micrograms); L (liters); ml (milliliters); µl (microliters); cm (centimeters); mm (millimeters); µm (micrometers); nm (nanometers); ° C. (degrees Centigrade); h (hours); min (minutes); sec (seconds); msec (milliseconds); xg (times gravity); Ci (Curies); OD (optical density); Dulbecco's phosphate buffered solution (DPBS); HEPES (N-[2-Hydroxyethyl]piperazine-N-[2-ethanesulfonic acid]); HBS (HEPES buffered saline); SDS (sodium dodecylsulfate); Tris-HCl (tris[Hydroxymethyl]aminomethane-hydrochloride); Klenow (DNA polymerase I large (Klenow) fragment); rpm (revolutions per minute); EGTA (ethylene glycol-bis(β-aminoethyl ether) N,N,N',N'-tetraacetic acid); EDTA (ethylenediaminetetraacetic acid); SPT+ (skin prick test positive); SPT− (skin prick test negative); ATCC (American Type Culture Collection, Rockville, Md.); Cedar Lane (Cedar Lane Laboratories, Ontario, Canada); Gibco/Life Technologies (Gibco/Life Technologies, Grand Island, N.Y.); Sigma (Sigma Chemical Co., St. Louis, Mo.); Pharmacia (Pharmacia Biotech, Piscataway, N.J.); Procter & Gamble (Procter and Gamble, Cincinnati, Ohio); Genencor (Genencor International, Palo Alto, Calif.); Endogen (Endogen, Woburn, Mass.); Cedarlane (Cedarlane, Toronto, Canada); Dynal (Dynal, Norway); Novo (Novo Industries A/S, Copenhagen, Denmark); Biosynthesis (Biosynthesis, Louisville, Tex.); TriLux Beta, (TriLux Beta, Wallac, Finland); DuPont/NEN (DuPont/NEN Research Products, Boston, Mass.); TomTec (Hamden, Conn.); and Stratagene (Stratagene, La Jolla, Calif.).

Peptides

All peptides were obtained from a commercial source (Mimotopes, San Diego, Calif.). For the I-MUNE® assay system described herein, 15-mer peptides offset by 3 amino acids that described the entire sequence of the proteins of interest were synthesized in a multipin format (See, Maeji et al., J. Immunol. Meth., 134:23-33 [1990]). Peptides were resuspended in DMSO at approximately 1 to 2 mg/ml, and stored at −70° C. prior to use. Each peptide was tested at least in duplicate, although for small peptide sets (e.g., Ber e 1), the peptides were routinely tested in triplicate. The results for each peptide were averaged and the stimulation index (SI) was calculated for each peptide.

Protein Sequences

Amino acid sequences from the following well-characterized industrial enzymes were tested and rank ordered using the methods of the present invention. The sequences of these proteins are publicly available from databases such as Medline. The proteins that are described herein in greatest detail include *B. lentus* subtilisin (Swissprot accession number P29600), BPN' Y217L (Swissprot accession number P00782), ALCALASE® enzyme (Swissprot accession number P00780), and alpha-amylase (Swissprot accession number P06278).

Human Donor Blood Samples

Volunteer donor human blood buffy coat samples were obtained from two commercial sources (Stanford Blood Center, Palo Alto, Calif., and the Sacramento Medical Foundation, Sacramento, Calif.). Buffy coat samples were further purified by density separation. Each sample was HLA typed for HLA-DR and HLA-DQ using a commercial PCR-based kit (Bio-Synthesis). The HLA DR and DQ expression in the donor pool was determined to not be significantly different from a North American reference standard (Mori et al., Transplant., 64:1017-1027 [1997]). However, the donor pool did show evidence of slight enrichments for ethnicities common to the San Francisco Bay Area.

Preparation of Dendritic Cells and CD4+ T-Cells

Monocytes were purified by adherence to plastic in AIM V medium (Gibco/Life Technologies). Adherent cells were cultured in AIM V media containing 500 units/ml of recombinant human IL-4 (Endogen) and 800 units/ml recombinant human GM-CSF (Endogen) for 5 days. On day 5, recombinant human IL-1α (Endogen) and recombinant human TNF-α (Endogen) were added to 50 units/ml and 0.2 units/ml, respectively. On day 7, the fully matured dendritic cells were treated with 50 ug/ml mitomycin C (Sigma) for 1 hour at 37° C. Treated dendritic cells were dislodged with 50 mM EDTA in PBS, washed in AIM V medium, counted, and resuspended in AIM V media at $2 \times 10^5$ cells/ml.

CD4+ T-cells were purified by negative selection from frozen aliquots of human peripheral blood mononuclear cells (PBMC) using Cellect CD4 columns (Cedarlane). CD4+ T-cell populations were routinely >80% pure and >95% viable as judged by trypan blue (Sigma) exclusion. CD4+ T-cells were resuspended in AIM V media at $2 \times 10^6$ cells per ml.

I-MUNE® Assay Conditions

CD4+ T-cells and dendritic cells were plated in round-bottomed 96 well format plates at 100 ul of each cell mix per well. Peptide was added to a final concentration of approximately 5 ug/ml in 0.25-0.5% DMSO. Control wells contained 0.5% DMSO without added peptide. Each peptide was tested in duplicate. Cultures were incubated at 37° C., in 5% $CO_2$ for 5 days. On day 5, 0.5 uCi of tritiated thymidine (NEN DuPont,) was added to each well. On day 6, the cultures were harvested onto glass fiber mats using a TomTec manual harvester (TomTec), then processed for scintillation counting. Proliferation was assessed by determining the average counts per minute (CPM) value for each set of duplicate wells (Tri-Lux Beta). This method is also described in U.S. Pat. No. 6,218,165 and Stickler et al., J. Immunother. 23: 654-660 (2000), both of which are herein incorporated by reference.

Data Analysis

For each individual buffy coat sample, the average CPM values for all of the peptides were analyzed. The average CPM values for each peptide were divided by the average CPM value for the control (DMSO only) wells to determine the "stimulation index" (SI). Donors were tested with each peptide set until an average of at least two responses per peptide were compiled. The data for each protein was graphed showing the percent responders to each peptide within the set. A positive response was collated if the SI value was equal to or greater than 2.95. This value was chosen as it approximates a difference of three standard deviations in a normal population distribution. For each protein assessed, positive responses to individual peptides by individual donors were compiled. To determine the background response for a given protein, the percent responders for each peptide in the set were averaged and a standard deviation was calculated. SI values for each donor were compiled for each peptide set, and the percent of responders reported. The average background response rate for each peptide set was calculated by averaging the percent response for all of the peptides in the set. Statistical significance was calculated using Poisson statistics for the number of responders to each peptide within the dataset. Different statistical methods were used as described herein. The response to a peptide was considered significant if the number of donors responding to the peptide was different from the Poisson distribution defined by the dataset with a p<0.05.

Peptide Binding Analysis

In addition to the above I-MUNE® assay, peptide binding assays were also performed. The peptide binding assay used during the development of the present invention is known in the art (Southwood et al., J. Immunol., 160:3363-3373 [1998]). Briefly, HLA-DR and -DQ molecules were purified from a panel of EBV transformed cell lines. A competition assay was performed with a characterized standard peptide, and the unknown peptide. The amount of unknown peptide required to compete 50% of the standard peptide binding was then determined (indicated as the $IC_{50}$).

Statistical Methods*

Statistical significance of peptide responses were calculated based on Poisson statistics. The average frequency of responders was used to calculate a Poisson distribution based on the total number of responses and the number of peptides in the set. A response was considered significant if p<0.05. In addition, two-tailed Student's t-tests with unequal variance, were performed. For epitope determination using data with low background response rates, a conservative Poisson based formula was applied:

$$= 1 - e\left(-n\left(1 - \sum \frac{\lambda^x e^{-\lambda}}{x!}\right)\right)$$

where n=the number of peptides in the set, x=the frequency of responses at the peptide of interest, and λ=the median frequency of responses within the dataset. For epitope determinations based on data with a high background response rate, the less stringent Poisson based determination $$1 - \left(\sum_{i=0}^{x} \frac{\lambda^x e^{-\lambda}}{x!}\right)$$

was used, where λ=the median frequency of responses in the dataset, and x=the frequency of responses at the peptide of interest.

In additional embodiments, the structure determination was calculated based on the following formula:

$$\sum \left| f(i) - \frac{1}{p} \right|$$

wherein Σ (upper case sigma) is the sum of the absolute value of the frequency of responses to each peptide minus the frequency of that peptide in the set; f(i) is defined as the frequency of responses for an individual peptide; and p is the number of peptides in the peptide set.

This equation returns a value between 0 and 2, which is equal to the "Structure Value." A value of 0 indicates that the results are completely without structure, and a value of 2.0 indicates all structure is highly structured around a single area. The closer the value is to 2.0, the more immunogenic the protein. Thus, a low value indicates a less immunogenic protein.

HLA Types within the Donor Pool

HLA-DR and DQ types were analyzed for associations with responses to defined epitope peptides. A Chi-squared analysis, with one degree of freedom was used to determine significance. Where an allele was present in both the responder and non-responder pools, a relative risk was calculated.

The HLA-DRB1 allelic expression was determined for approximately 185 random individuals. HLA typing was performed using low-stringency PCR determinations. PCR reactions were performed as directed by the manufacturer (Bio-Synthesis). The data compiled for the Stanford and Sacramento samples were compared the "Caucasian" HLA-DRB1 frequencies as published (See, Marsh et al., *HLA Facts Book, The*, Academic Press, San Diego, Calif. [2000], page 398, FIG. 1). The donor population in these communities is enriched for HLA-DR4 and HLA-DR15. However, the frequencies of these alleles in these populations are well within the reported range for these two alleles (5.2 to 24.8% for HLA-DR4 and 5.7 to 25.6% for HLA-DR15). Similarly, for HLA-DR3, -DR7 and DR11, the frequencies are lower than the average Caucasian frequency, but within the reported ranges for those alleles. Also of note, HLA0DR15 is found at a higher frequency in ethnic populations that are heavily represented in the San Francisco Bay Area.

Example 1

Compiled Results for Four Known Respiratory Allergens

In this Example, the results obtained using the I-MUNE® assay and analysis methods of the present invention described above, to test four known respiratory allergens are described.

A. Alpha Amylase

In these experiments, 82 individuals were tested with peptides derived from the alpha amylase sequence. The background response to peptides in this set was 2.80+/−3.69%, well within the overall average obtained in tests with 11 industrial enzymes of 3.16+/−1.57 (data not shown). Prominent responses were noted to amino acids 34-48, 160-174, and 442-456 of alpha amylase (See, FIG. 2). All three of these responses were highly significant above the background response ($p<0.0001$).

B. *B. lentus* Subtilisin

In these experiments, 65 individuals were tested with two replicate peptide sets for this protein and the results were compiled. The background for this peptide set was found to be 3.45+/−2.90%, but within the established range. Prominent responses were noted at amino acids 160-174 ($p=0.0003$) (See, FIG. 3).

C. BPN' Y217L

In these experiments, 113 individuals were tested with two peptide sets. The compiled average for this dataset was 3.62%. Prominent responses were noted at amino acids 70-84 and 109-123 (See, FIG. 4). A region of responses was also noted around amino acid 154.

D. ALCALASE® Enzyme

In these experiments, 92 individuals were tested with peptides derived from this enzyme. The background response to this protein was found to be low (2.35%). The same peptide set was tested in two temporally spaced analyses, and the data were compiled. In addition, there were significantly more peptides returning no response within the set for this protein. A prominent response was noted at amino acids number 19-33 ($p<0.0001$) (See, FIG. 5).

Example 2

Structure Calculations

This Example describes the structure values obtained for the four enzymes tested. Structure values are dependent on the number of donors tested. A zero response rate across most of the dataset results in a structure value of ~1.0. The same number of responses at each peptide yields a structure value of 0. Therefore, it is important to test a peptide set until responses across the majority of the dataset are accumulated, in order for the data to accurately reflect responsivity to particular peptides and peptide regions. The structure value decreases with increasing numbers of donors tested until a plateau level is reached, usually between 2-3 responses per peptide (See, FIG. 6). The plateau structure value must be used for comparing structure values.

For each of the enzymes tested, the compiled responses were used to calculate structure within the dataset. The structure values were: 0.81 for amylase, 0.72 for ALCALASE® enzyme, 0.64 for *B. lentus* subtilisin, and 0.53 for BPN' Y217L, as shown in Table 1.

TABLE 1

Structure Determination for Four Respiratory Allergens

| Enzyme | Peptides | n | Responses per peptide | Number of epitope regions | Structure value |
|---|---|---|---|---|---|
| Amylase | 157 | 82 | 2.29 | 3 | 0.81 |
| *B. lentus* subtilisin | 86 | 65 | 2.24 | 1 | 0.64 |
| ALCALASE ® | 88 | 92 | 2.16 | 1 | 0.72 |
| BPN'Y217L | 88 | 113 | 3.65 | 2 | 0.53 |

These results indicate that there is more activity induced by the amylase peptide set, when CD4+ T cell activation is measured by a level of proliferation resulting in an SI of 2.95 or greater, as compared to activity measured using the other peptide sets. The result for BPN' Y217L indicates that the peptide set derived from the sequence of this protein was the least active, with the lowest amount of structure. The structure values rank order the four tested proteins as:

amylase>ALCALASE® enzyme>*B. lentus* subtilisin>BPN'Y217L

Example 3

Comparison to Animal Models

As indicated above, two animal models have been used for the prediction of allergenicity and immunogenicity of industrial proteins. Thus, in this Example, comparisons made between these two animal models and the methods of the present invention are described. Both the guinea pig (GPIT) and BDF1 mouse (MINT) models rank the proteins in the order: amylase>ALCALASE® enzyme>*B. lentus* subtilisin>BPN' Y217L. However, the relative values differ. FIG. 7 shows the structure values graphed versus the GPIT (Panel A) and MINT (Panel B) potency values. Human cell-based structure data obtained from using the methods of the present invention indicate a correlation with both methods ($R^2$ values of 0.86 and 0.84, respectively).

Example 4

Structure Values of Additional Proteins

In this Example, structure values obtained for additional proteins are described. For example, structure values were calculated for Ber e 1 (i.e., the major allergen found in Brazil nuts), human interferon-beta (IFN-β), human thrombopoietin (Tpo), a mouse VH 36-60 family member and human β2-microglobulin (See, Table 2).

TABLE 2

Structure Values for Selected Additional Proteins

| | Peptides | n | Average Background | Response per peptide | Number of epitope regions | Structure value |
|---|---|---|---|---|---|---|
| hTpo | 52 | 99 | 2.56 | 2.54 | 1 | 0.65 |
| hIFN-B | 52 | 88 | 3.17 | 2.79 | 1 | 0.75 |
| Ber e 1 | 27 | 92 | 4.27 | 3.92 | 2 | 0.66 |
| Mouse Vh 36-60 family | 35 | 74 | 7.0 | 5.23 | 0 | 0.38 |
| B2-microglobulin | 36 | 87 | 3.9 | 3.39 | 0 | 0.39 |

Human IFN-β, Tpo and Ber e 1 are all known to induce immune responses in humans (See, Scagnolari et al., J. Interferon Cytokine Res., 22:207-213 [2002]; and Sicherer and Sampson, Curr. Opin. Pediatr., 12:567-573 [2000]; and Li et al., Blood 98:3241-3248 [2001]). The structure values for IFN-β, Tpo and Ber e 1 are all comparatively high. The value for the mouse VH region is comparatively low, suggesting that this protein is comparatively non-immunogenic. This result is consistent with a structural analysis of potential immunogenicity of the mouse heavy chain families (See, Olsson et al., [1991] supra). In addition, the result for β2-microglobulin is low, consistent with tolerance induction to this ubiquitously expressed protein [Guery et al., [1995] supra).

Example 5

Population-Based Immune Responses

In this Example, experiments conducted to assess the population-based immune responses of a population are described. The donor bloods were obtained from Stanford and Sacramento, as indicated above, as this population has a distribution that is not statistically different from the general "Caucasian" population in the U.S. Samples from the these donor bloods were tested in the I-MUNE® assay system described above. The structure values were calculated and collated for every protein tested in the I-MUNE® assay, for which there were more than two responses per peptide. The proteins tested were Ber e 1 (Brazil nut allergen), scFv (single-chain V region of an antibody; the VH and VL segments); BLA (β-lactamase); IFN-B (interferon-beta), FNA (subtilisin-BPN' Y217L), α-amylase, E6 (human papillomavirus E6 protein in HPV strains 16, 18, 31, and 33), E7 (HPV E7 protein in HPV strains 16, 18, 31, 33, 45 and 52), eglin (leech protease inhibitor; GenBank Accession No. CAA25380); RECK (human protease inhibitor; actually a small domain within the 971 amino acid RECK protein [GenBank Accession No. NP_066934] was tested; staphylokinase, TPO (human thrombopoeitin), ecotin (serine protease inhibitor from *E. coli* K12; GenBank Accession No. NP_416713; ALCALASE® enzyme, savinase, human β-2 microglobulin, sTNFR1 (soluble tumor necrosis factor receptor 1). The results of these experiments are shown in Table 3. In this Table, the data indicate how many donors responded (i.e., mounted a proliferative response with an SI>2.95) to each peptide in the pepset.

TABLE 3

Results

| Test Protein | Structure Value | Response/Peptide | Background % |
|---|---|---|---|
| Ber e 1 | 0.66 | 3.93 | 4.26 |
| scFv | 0.39 | 3.96 | 4.9 |
| BLA | 0.56 | 2.62 | 3.27 |
| IFN-B | 0.75 | 2.79 | 3.17 |
| FNA | 0.65 | 3.61 | 3.65 |
| Amylase | 0.81 | 2.29 | 2.79 |
| E6 16 | 0.72 | 3.92 | 7.12 |
| 18 | 0.79 | 2.32 | 4.23 |
| 31 | 0.53 | 3.26 | 4.66 |
| 33 | 0.68 | 1.97 | 2.83 |
| E7 16 | 0.66 | 3.9 | 4.33 |
| 18 | 0.44 | 3.19 | 3.55 |
| 31 | 0.78 | 3.1 | 5.26 |
| 33 | 0.54 | 2.55 | 4.32 |
| 45 | 0.76 | 2.44 | 3.75 |
| 52 | 0.59 | 3.69 | 5.68 |
| Eglin | 0.43 | 4.9 | 5.57 |
| RECK | 0.39 | 4.1 | 4.64 |
| Staphylokinase | 0.44 | 4.48 | 6.22 |
| Tpo | 0.65 | 2.24 | 2.53 |
| Ecotin | 0.64 | 3.98 | 5.69 |
| Alcalase | 0.72 | 2.16 | 2.35 |
| GG36 | 0.65 | 2.24 | 3.45 |
| β-2 microglobulin | 0.39 | 3.38 | 3.9 |
| sTNFR1 | 0.47 | 2.9 | 4.2 |

Four regions of exposure and immune response level were determined. FIG. 10 provides a graph showing the relative structure value and background percent for these proteins. Quadrant "1" reflects the number of individuals in the population who have not been exposed to the test protein (represented by 1 data point [◊]), while quadrant "2" reflects the number of individuals in the population who have been exposed to the test protein, wherein the exposure is more recent, frequent, and/or qualitatively more immunogenic, quadrant "3" reflects the number of individuals in the population who have been tolerized to the test protein and/or the test protein is non-immunogenic, and quadrant "4" reflects the number of individuals in the population who have been exposed to the test protein, but the exposure was long-past or infrequent, and/or the test protein is qualitatively less immunogenic.

The proteins in quadrant "1" were BLA, IFN-β, FNA, amylase, HPV33 E6, HPV45 E7, TPO, ALCALASE® enzyme, and GG36; while the proteins in quadrant "2" were Ber e 1, HPV16 E6, HPV18 E6, HPV31 E6, HPV16 E7, HPV31 E7, HPV33 E7, HPV45 E7, and HPV52 E7, and ecotin; the proteins in quadrant "3" were HPV18 E7, and β-2 microglobulin; and the proteins in quadrant "4" were scFv, eglin, RECK, staphylokinase, and sTNFR1. Thus, it is clear that the present invention provides means to assess the population-based immune responses of any protein.

Example 6

Creation of Variants with Reduced Structure Values

In this Example, methods for the creation of variants with reduced structural values are provided. As an example of how the structure analysis finds use in calculating the overall immunogenicity of variant proteins designed to reduce immunogenicity in humans, a structure value was calculated for a variant where the prominent responses to amino acids 70-84 and 109-123 in BPN' Y217L were reduced to background level responses. A limited dataset of 48 individuals was tested using peptide variants to the 70-84 and 109-123 regions of BPN' Y217L. Responses to the variants were found to be at background level. The complete dataset of 113 individuals was modified for structure calculations by reducing the responses to 70-84 and 109-123 to background levels. The structure was calculated this way in order to predict what the structure value would have been if 113 individuals had been tested along with the parent molecule. Since responses were removed from the calculation, an equivalent number of responses were scattered randomly through the dataset in order to maintain the same overall rate of response. The structure value for the modified protein variant was calculated to be 0.40 (See, Table 4).

TABLE 4

Structure Calculations for a Potential Protease Variant

| Protease | Prominent Epitope | Structure Value |
|---|---|---|
| BPN' Y217L | 2 | 0.53 |
| BPN' variant | 0 | 0.40 |

In addition, in vitro data indicated that the protease variant with the lower structure value induced less proliferation. In these experiments, PMBC from thirty community donors were tested parametrically with either the whole protein parent enzyme (BPN' Y217L) or the variant protease. The enzymes were inactivated, and tested over a dose range from 5 to 40 ug/ml. The highest Si values reached for each protein are shown in FIG. 9. The parent protease had a structure value of 0.53, and the variant had a structure value of 0.40. The difference between optimal SI values for the two proteins tested on these thirty donors was significant, with a two-tailed parametric t-test value of $p<0.01$. These results indicate that reducing the structure value from 0.53 to 0.40 has a profound effect on the in vitro antigenicity of the molecule.

In preferred methods of the present invention, when variant proteins are compared to a parent protein either in vitro or in vivo, the proteins are preferably compared at the same dose, in the formulation, in a matched set of donors and over the same dose curve. The variant proteins should retain the parent protein's general physical and structural properties, such as stability and activity. Additionally, the structure analysis precludes any processing differences between the parent protein and its variants.

Example 7

Designation of CD4+ T-Cell Epitopes

In this Example, data from unexposed and exposed donors are presented. These data are provided in addition to those in the above Examples.

Unexposed Donors

Sixty-five donors were tested with a set of 15-mer peptides synthesized to cover the sequence of *B. lentus* subtilisin. The percent response to each peptide for the 65 donors is shown in FIG. 12, Panel A. A prominent response at position #54, corresponding to amino acids 160-174 is apparent. Another region of prominence is also apparent at peptide positions 23 and 31 (amino acids 67-81 and 91-105). The frequency of responses to the peptides in the set is shown in FIG. 12, Panel B. It is clear that the frequency of responses to the peptide at amino acids 160-174 is different than the frequency of responses to other peptides in the set. However, the significance of the responses at amino acids 67-81 and 91-105 must be determined. Significance was determined by establishing Poisson distributions for the frequency data then determining the probability that a dataset containing the number of values represented by the number of peptides in the set would include as its highest member the value in question. For the peptide represented by amino acids 160-174, this probability was $p=0.0004$. For the other two peptides, the probability was $p=0.50$.

As a test of the epitope selection criteria, a set of seven donors verified to have been exposed to *B. lentus* subtilisin by skin-prick testing were also tested using the I-MUNE® assay system described herein. The number of responses at each peptide is shown for all seven donors (See, FIG. 13). Only one peptide was found to elicit more than two responses. The three responders to the amino acids 163-177 peptide included both of the HLA-DR2(15) positive donors. An association with response to this peptide and HLA-DR2(15) was noted previously (Stickler et al., J. Immunother., 23:654-660 [2000]). There were two donors that responded to six peptide regions, including the 67-81 region. No other peptide from the exposed donor data was prominent in the unexposed donor data. The 67-81 region has high homology (14/15 amino acid identity) to a known CD4+ T cell epitope in a related protease, and half of these donors were also SPT+ to this second protease. Therefore, as a conservative estimate one verified epitope was found in the unexposed donor population, and this epitope is found to be prominent in a set of epitopes recognized by verified protein-exposed donors.

Similar results were observed for another related subtilisin from *B. amyloliquifaciens*. Two prominent epitope regions that were highly significant were described, and these two epitopes were also found in a set of verified SPT+ donors (data not shown). As above, more prominent epitope regions were seen in compiled data from exposed donors, and the epitope peptides defined in the unexposed donor set were a subset of these.

Memory Responses

The I-MUNE® assay described above was performed on a set of peptides derived from the sequence of staphylokinase. Staphylokinase was selected for these experiments due to the fact that the general population accumulates specific responses to this protein over time (See, Warmerdam et al., J. Immunol., 168:155-161 [2002]). A set of 72 community donors was tested in the I-MUNE® assay system of the present invention with this protein. The responses to peptides in the staphylokinase set are shown in FIG. 14, Panel A. There are no clearly prominent responses in the staphylokinase data set. This is clearly shown in the frequency data (See, FIG. 4, Panel B) where, unlike the frequency data for *B. lentus* subtilisin, there are no individual peptides that accumulated responses at a rate that was clearly distinct from the distribution of responses to the other peptides. However, the prominent response rates at positions 5 (amino acids 13-27), 20 and 21 (amino acids 58-75), 29 (amino acids 85-99) and 36 (amino acids 106-120) are of interest. The dataset shows an average response of 4.48 responses per peptide (background=6.22%; See, Table 5, below). If this value is used to define the median of a Poisson distribution, a less conservative analysis indicates that the response frequencies displayed by all of the prominent peptides outlined above are significant (p<0.05). This analysis is much less conservative than the analysis used to assign significance to epitopes found in the unexposed donors, as the Poisson distribution is defined by the median background value, and difference from this value is used to determine significance.

TABLE 5

Background Values for Proteins with Presumed Donor Pre-exposure

|  | Donors tested | Expected responses/peptide[b] | Responses/peptide found[c] | Background +/− sd[d] | t-test[e] |
|---|---|---|---|---|---|
| 11 industrial enzymes | n.a.[a] | n.a. | n.a. | 3.15 +/− 1.57 | n.a. |
| HPV 16 E6 | 55 | 1.65 | 3.92 | 7.12 +/− 6.48 | P = 0.0003 |
| HPV 18 E6 | 55 | 1.65 | 2.32 | 4.23 +/− 4.25 | P = 0.16 |
| Ber e 1 | 92 | 2.77 | 3.92 | 4.26 +/− 4.05 | P = 0.22 |
| staphylokinase | 72 | 2.17 | 4.48 | 6.22 +/− 3.47 | P = 0.0001 |
| IFN-beta | 88 | 2.65 | 2.79 | 3.17 +/− 3.28 | n.d.[f] |
| Tpo | 99 | 2.99 | 2.51 | 2.54 +/− 2.23 | n.d. |
| TNF-R1 | 69 | 2.08 | 1.54 | 2.23 +/− 1.95 | n.d. |

In this Table,
[a]indicates "not applicable";
[b]indicates the expected number of responses per peptide for the number of donors tested, based on the data from the 11 industrial proteins shown in FIG. 11;
[c]indicates the response per peptide value determined experimentally for the protein tested;
[d]indicates the background response value for the protein tested;
[e]indicates the two-tailed, unequal variance t-test comparing the background values for the 11 industrial enzymes to the background response of the protein tested; and
[f]indicates "not determined."

The five epitope peptides identified in the I-MUNE® assay were compared to published epitopes defined using cloned CD4+ T cell lines from donors with antigen-specific responses to staphylokinase (See, FIG. 15).

The regions defined using cloned T cells from 10 donors, D1, F2, C3, and D4 contain core sequences (common peptide sequence between the majority of the responding clones) that correspond to I-MUNE® assay-identified peptides 5, 20, 21 and 36 respectively. The I-MUNE® assay identified an epitope peptide at position 29 (amino acids 85-99) that was not detected using CD4+ T cell clones. This peptide associated with the presence of HLA-DR5(11). Only one donor who provided clones for the CD4+ T cell clone study carried this allele, and therefore it may have been missed. Alternatively, this peptide may not be processed from staphylokinase, and the result would therefore be a false positive within the I-MUNE® assay dataset. However, the carboxy terminus of the protein, region A5, was previously reported as being recognized by T cell clones (See, Warmerdam et al., supra). The I-MUNE® assay located an epitope in a subset of the region, peptide 36, which corresponded with the adjacent D4 region. Overall, the alignment between the epitopes found using the less conservative epitope designation described and the published epitopes was excellent. In addition, the HLA associations reported are consistent between the two datasets (See, FIG. 15).

Negative Control

As a negative control, human β2-microglobulin was also tested in the I-MUNE® assay with samples from 87 community donors. This protein was selected as a negative control as it is present as part of the HLA class I molecule on the surface of all somatic cells. In addition, β2-microglobulin is expressed in the thymus during T cell development. Both central and peripheral tolerance mechanisms should affect the T cell repertoire, removing any CD4+ T cell with significant cross-reactivity to β2-microglobulin-derived peptides (See, Guery et al., J. Immunol., 154:545-554 [1995]). Finally, there is minimal allelic variation in this molecule. One allelic variant was found in a database search (not shown). The results are shown in FIG. 16. The average background response to β2-microglobulin was 3.90+/−1.82 percent. The percent responses to the peptides are shown in FIG. 16, Panel A, and the frequency of responses is shown in FIG. 16, Panel B. None of the peptide responses were significant based on the statistical method for an unexposed donor population with a low background response rate.

Reproducibility of Response Rates

The reproducibility of epitope peptide responses was determined by repeat testing of epitope peptides. Peptides were synthesized at least twice and were tested on multiple discrete groups of donors. The donor number tested for each test ranged from 27 to 103 donors. The average percent responses to the peptides were compared. The results are shown in Table 6. The average coefficient of variance (CV) for the four epitope peptides was 20%, and the median value was 21%. The range of CVs was 9.3 to 27%. These values compare favorably to other human cell-based ex vivo assays (Keilholz et al., J. Immunother., 25:97-138 [2000]; and Asai et al., Clin. Diagn. Lab. Immunol., 7:145-154 [2000]). In Table 6, "s.d." is standard deviation, "s.e." is standard error, and "s.d./average*100)" is the percent CV. The average and the median values for the four peptides are shown.

TABLE 6

Reproducibility of Epitope Peptide Responses

|  | Number of tests | Average | s.d. | s.e. | % CV |
|---|---|---|---|---|---|
| IFN-B | 3 | 16.41 | 1.53 | 0.88 | 9.32 |
| TPO | 3 | 9.18 | 1.83 | 1.06 | 19.99 |
| BPN'Y217L #24 | 4 | 11.69 | 2.71 | 1.35 | 23.18 |
| BPN'Y217L#37 | 4 | 12.91 | 3.51 | 1.76 | 27.19 |
|  |  |  |  | Average for all | 19.92 |
|  |  |  |  | Median | 21.59 |

Epitopes Confirmed with Binding Studies

The $IC_{50}$ for HLA class II protein binding was determined for peptide epitopes defined by the in two related industrial bacterial proteases (See, FIG. 17). The peptides were tested in a competition assay for binding to 18 different HLA-DR and -DQ proteins. The prominent epitope in *B. lentus* subtilisin was found to bind a range of HLA-DR and -DQ molecules in two different frames (160-174 and 157-171), indicating promiscuous binding. Peptide binding to HLA-DR2(15) was found to be excellent, with an $IC_{50}$ of 127 nM. Only HLA-DR1 displayed a lower $IC_{50}$ value. Of the two epitopes defined by the I-MUNE® assay in *B. amyloliquifaciens* subtilisin BPN' Y217L, the second epitope (amino acids 109-123) was found to be promiscuous in both the HLA analysis and in the binding analysis described in this Example. The first epitope (amino acids 70-84) also binds most HLA class II molecules tested, but it binds HLA-DR6(13) with an IC50 of 0.69 nM. This likely explains the association seen in the data for a response to this peptide with HLA-DR6(13) donors (p=0.00015; relative risk=7.22, n=113 donors tested). Those results with values less than 500 nM were considered to be good binders and are highlighted in bold in FIG. 17. Also, in this Figure, degeneracy indicates the number of HLA Class II proteins that bind with an $IC_{50}$ of less than 500 nM out of the 18 total alleles tested.

The invention claimed is:

1. A method for ranking the relative immunogenicity of a first protein and at least one additional protein, comprising the steps of:
    (a) preparing a first pepset from a first protein and preparing at least one additional pepset from each of said at least one additional protein;
    (b) obtaining from a single human blood source a solution comprising dendritic cells and a solution of naïve CD4+ T-cells;
    (c) differentiating said dendritic cells to produce a solution of differentiated dendritic cells;
    (d) combining said solution of differentiated dendritic cells and said naïve CD4+ T-cells with each peptide in said first pepset, individually; and separately
    (e) combining said solution of differentiated dendritic cells and said naïve CD4+ T-cells with each peptide in each of said pepsets, individually from said at least one additional protein;
    (f) measuring proliferation of said T-cells in said steps (d) and (e), to determine the responses to peptides in each of said first and said additional pepsets;
    (g) compiling the responses of said T-cells in step (f) for said first protein and said at least one additional protein;
    (h) determining the structure value of said compiled responses of step (g) for said first protein and said at least one additional protein using a formula for calculating total variation distance to the uniform or entropy of the distribution; and
    (i) comparing the structure value obtained for said first protein with the structure value for said at least one additional protein to determine the relative immunogenicity ranking of said first protein and said at least one additional protein.

2. The method of claim 1, wherein the protein having the lowest structure value is ranked as less immunogenic than the protein having the higher structure value.

3. The method of claim 1, wherein said first protein and at least one additional protein are selected from the group consisting of enzymes, hormones, cytokines, antibodies, structural proteins, and binding proteins.

4. The method of claim 1, wherein a stimulation index value between about 2.7 and about 3.2 is obtained for a peptide of said first pepset, wherein the stimulation index refers to the T-cell proliferative response in the presence of the peptide measured in step (f) compared to T-cell proliferative response for a control solution without the peptide.

5. The method of claim 1, wherein a stimulation index value between about 2.7 and about 3.2 is obtained for a peptide of said at least one additional pepset, wherein the stimulation index refers to the T-cell proliferative response in the presence of the peptide measured in step (f) compared to T-cell proliferative response for a control solution without the peptide.

6. The method of claim 4, wherein the stimulation index is between about 2.95 and about 3.2.

7. The method of claim 5, wherein the stimulation index is between about 2.95 and about 3.2.

8. The method of claim 1, wherein at least one additional human blood source is used in step (b), and wherein said dendritic cells and a solution of naïve CD4+ T-cells obtained from said human blood sources are tested in parallel.

9. The method of claim 8, wherein the structure values obtained for each of said human blood sources and said proteins are compared.

10. The method of claim 9, wherein the structure values and background percent response values of said proteins are used to rank said proteins.

11. A method for ranking the relative immunogenicity of two proteins, wherein said second protein is a protein variant of said first protein, comprising the steps of:
    (a) preparing a first pepset from a first protein and a second pepset from a second protein;
    (b) obtaining from a single human blood source a solution of dendritic cells and a solution of naïve CD4+ T-cells;
    (c) differentiating said dendritic cells, in said solution of dendritic cells, to produce a solution of differentiated dendritic cells;
    (d) combining said solution of differentiated dendritic cells and said naïve CD4+ T-cells with each peptide in said first pepset, individually; and separately
    (e) combining said solution of differentiated dendritic cells and said naïve CD4+ T-cells with each peptide in said second pepset, individually;
    (f) measuring proliferation of said T-cells in said steps (d) and (e), to determine the responses to peptides in each of said first and second pepsets;
    (g) compiling the responses of said T-cells in step (f) for said first protein and said second protein;
    (h) determining the structure value of said compiled responses of step (g) for said first protein and said second protein using a formula for calculating total variation distance to the uniform or entropy of the distribution; and
    (i) comparing the structure value obtained for said first protein with the structure value for said second protein to determine the relative immunogenicity ranking of said first protein and said second protein.

12. The method of claim 11, wherein said second protein is ranked as less immunogenic than said first protein.

13. The method of claim 11, wherein said first protein is ranked as less immunogenic than said second protein.

14. The method of claim 11, wherein said first and second proteins are selected from the group consisting of enzymes, hormones, cytokines, antibodies, structural proteins, and binding proteins.

15. The method of claim 11, wherein a stimulation index value between about 2.7 and about 3.2 is obtained for a peptide of said first pepset, wherein the stimulation index refers to the T-cell proliferative response in the presence of the peptide measured in step (f) compared to T-cell proliferative response for a control solution without the peptide.

16. The method of claim 11, wherein a stimulation index value between about 2.7 and about 3.2 is obtained for a peptide of said second pepset, wherein the stimulation index refers to the T-cell proliferative response in the presence of the peptide measured in step (f) compared to T-cell proliferative response for a control solution without the peptide.

17. The method of claim 15, wherein the stimulation index is between about 2.95 and about 3.2.

18. The method of claim 16, wherein the stimulation index is between about 2.95 and about 3.2.

19. The method of claim 11, wherein the proliferation of said T-cells in step (e) is at a background level.

20. The method of claim 11, wherein at least one additional human blood source is used in step (b), and wherein said dendritic cells and a solution of naïve CD4+ T-cells obtained from said human blood sources are tested in parallel.

21. The method of claim 20, wherein the structure values obtained for each of said human blood sources and said proteins are compared.

22. The method of claim 21, wherein the structure values and background percent response values of said proteins are used to rank said proteins.

23. A method for ranking the relative immunogenicity of a first protein and at least one variant protein, comprising the steps of:
   (a) preparing a first pepset from a first protein and pepsets from each of said variant proteins;
   (b) obtaining from a single human blood source a solution comprising dendritic cells and a solution of naïve CD4+ T-cells;
   (c) differentiating said dendritic cells to produce a solution of differentiated dendritic cells;
   (d) combining said solution of differentiated dendritic cells and said naïve CD4+ T-cells with each peptide in said first pepset, individually; and separately
   (e) combining said solution of differentiated dendritic cells and said naïve CD4+ T-cells with each peptide in each pepset prepared from said variant proteins, individually;
   (f) measuring proliferation of said T-cells in said steps (d) and (e), to determine the responses to peptides in said first pepset and each pepset from said variant proteins;
   (g) compiling the responses of said T-cells in step (f) for said first protein and said variant proteins;
   (h) determining the structure value of said compiled responses of step (g) for said first protein and said variant proteins using a formula for calculating total variation distance to the uniform or entropy of the distribution; and
   (i) comparing the structure value obtained for said first protein with the structure values for said variant proteins to determine the relative immunogenicity ranking of said first protein and said variant proteins.

24. The method of claim 23, wherein at least one of said variant proteins is ranked as less immunogenic than said first protein.

25. The method of claim 23, wherein said first protein is ranked as less immunogenic than at least one of said variant proteins.

26. The method of claim 23, wherein said first and said variant proteins are selected from the group consisting of enzymes, hormones, cytokines, antibodies, structural proteins, and binding proteins.

27. The method of claim 23, wherein a stimulation index value between about 2.7 and about 3.2 is obtained for a peptide of said first pepset, wherein the stimulation index refers to the T-cell proliferative response in the presence of the peptide measured in step (f) compared to T-cell proliferative response for a control solution without the peptide.

28. The method of claim 23, wherein a stimulation index value between about 2.7 and about 3.2 is obtained for a peptide of said pepsets prepared from the variant proteins, wherein the stimulation index refers to the T-cell proliferative response in the presence of the peptide measured in step (f) compared to T-cell proliferative response for a control solution without the peptide.

29. The method of claim 27, wherein the stimulation index is between about 2.95 and about 3.2.

30. The method of claim 28, wherein the stimulation index is between about 2.95 and about 3.2.

31. The method of claim 23, wherein the proliferation of said T-cells in step (e) for at least one variant protein is at a background level.

32. The method of claim 23, wherein at least one additional human blood source is used in step (b), and wherein said dendritic cells and a solution of naïve CD4+ T-cells obtained from said human blood sources are tested in parallel.

33. A method for determining the immune response of a test population against a test protein, comprising the steps of:
   (a) preparing a pepset from said test protein;
   (b) obtaining a plurality of solutions comprising human dendritic cells and a plurality of solutions of naïve human CD4+ T-cells, wherein said solutions of human dendritic cells and solutions of naïve human CD4+ T-cells are obtained from a plurality of individuals within said test population;
   (c) differentiating said dendritic cells to produce a plurality of solutions comprising differentiated dendritic cells;
   (d) combining said plurality of said solutions of differentiated dendritic cells and said solutions of naïve CD4+ T-cells with each peptide in said pepset, individually, wherein each of said solutions of differentiated dendritic cells and said solutions of naïve CD4+ T-cells are from one individual within said test population are combined; and wherein said combining is conducted separately for said solutions of differentiated dendritic cells and said solutions of naïve CD4+ T-cells obtained from each individual within said test population;
   (e) measuring proliferation of each of said T-cells from each individual within said test population in step (d), to determine the responses to each peptide in each of said pepsets, individually;
   (f) compiling the responses of said T-cells in step (e) for said test protein for each of said individuals;
   (g) determining the structure value of said compiled responses of step (f) for said test protein for each of said test individuals using a formula for calculating total variation distance to the uniform or entropy of the distribution; and
   (h) determining the-immune response of said plurality of individuals within said test population to said test protein.

34. The method of claim 33, wherein said test protein comprises at least two test proteins, and wherein the method of claim 33 is conducted separately for each of said at least two proteins.

35. The method of claim 33, wherein immune responses of said plurality of said individuals in said test population to said test protein are compared.

36. The method of claim 35, further comprising the step of ranking the structure values and background percent response values of said test proteins to rank the immune response of said test population to said test proteins.

37. The method of claim 33, wherein said test protein is modified prior to conducting the step a), to produce a variant protein that exhibits a reduced immunogenic response in said test population.

* * * * *